US012758616B2

(12) United States Patent
Copik et al.

(10) Patent No.: US 12,758,616 B2
(45) Date of Patent: Oct. 13, 2026

(54) METHOD OF TREATING VIRAL INFECTIONS WITH NK CELLS TREATED WITH PM21 PARTICLES

(71) Applicants: University of Central Florida Research Foundation, Inc., Orlando, FL (US); Research Institute at Nationwide Children's Hospital, Columbus, OH (US)

(72) Inventors: Alicja Copik, Casselberry, FL (US); Jeremiah Oyer, Longwood, FL (US); Nitin Chakravarti, Columbus, OH (US); Dean Anthony Lee, Canal Winchester, OH (US)

(73) Assignees: RESEARCH INSTITUTE AT NATIONWIDE CHILDREN'S HOSPITAL, Columbus, OH (US); UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 683 days.

(21) Appl. No.: 18/201,572

(22) Filed: May 24, 2023

(65) Prior Publication Data

US 2023/0293585 A1 Sep. 21, 2023

Related U.S. Application Data

(62) Division of application No. 16/489,129, filed as application No. PCT/US2018/020187 on Feb. 28, 2018, now Pat. No. 11,696,927.

(60) Provisional application No. 62/464,747, filed on Feb. 28, 2017.

(51) Int. Cl.

| | |
|---|---|
| ***A61K 38/20*** | (2006.01) |
| ***A61K 40/10*** | (2025.01) |
| ***A61K 40/15*** | (2025.01) |
| ***A61K 40/42*** | (2025.01) |
| ***C12N 5/0783*** | (2010.01) |

(52) U.S. Cl.

CPC .............. *A61K 38/20* (2013.01); *A61K 40/10* (2025.01); *A61K 40/15* (2025.01); *A61K 40/42* (2025.01); *C12N 5/0646* (2013.01); *A61K 2239/31* (2023.05); *A61K 2239/38* (2023.05); *A61K 2239/48* (2023.05); *C12N 2501/2302* (2013.01); *C12N 2501/2318* (2013.01)

(58) Field of Classification Search

CPC ........ A61K 38/20; A61K 40/10; A61K 40/15; A61K 35/17; A61P 31/12

See application file for complete search history.

(56) References Cited

U.S. PATENT DOCUMENTS

| | | | | |
|---|---|---|---|---|
| 8,926,964 B2 * | 1/2015 | Hariri | A61K 40/15 435/377 |
| 2013/0287751 A1 | 10/2013 | Kaufman et al. | |
| 2014/0023626 A1 | 1/2014 | Peled et al. | |
| 2014/0170120 A1 | 6/2014 | Sackstein | |
| 2015/0190471 A1 | 7/2015 | Copik et al. | |
| 2015/0225697 A1 * | 8/2015 | Law | A01N 1/10 435/372 |

FOREIGN PATENT DOCUMENTS

| | | |
|---|---|---|
| WO | 2004094619 A1 | 11/2004 |
| WO | 2005017115 | 2/2005 |
| WO | WO 2006029010 * | 3/2006 |
| WO | 2016007506 | 1/2016 |
| WO | 2016069607 | 5/2016 |

OTHER PUBLICATIONS

Scheper et al. Hunting for clinical translation with innate-like immune cells and their receptors. Leukemia 28, 1181-1190, 2014. (Year: 2014).*

PCT/US2018/020187; International Search Report and Written Opinion dated May 16, 2018, 7 pages.

Altvater B, Landmeier S, Pscherer S, Temme J, Schweer K, Kailayangiri S, et al. 2B4 (CD244) signaling by recombinant antigen-specific chimeric receptors costimulates natural killer cell activation to leukemia and neuroblastoma cells. Clin Cancer Res 2009;15:4857-66.

Bachanova V, Cooley S, Defor TE, Verneris MR, Zhang B, McKenna DH, et al. Clearance of acute myeloid leukemia by haploidentical natural killer cells is improved using IL-2 diphtheria toxin fusion protein. Blood 2014;123:3855-63.

Berg M, Lundqvist A, McCoy P, Jr., Samsel L, Fan Y, Tawab A, et al. Clinical-grade ex vivo-expanded human natural killer cells up-regulate activating receptors and death receptor ligands and have enhanced cytolytic activity against tumor cells. Cytotherapy 2009;11:341-55.

Cany J, van der Waart AB, Tordoir M, Franssen GM, Hangalapura BN, de Vries J, et al. Natural killer cells generated from cord blood hematopoietic progenitor cells efficiently target bone marrow-residing human leukemia cells in NOD/SCID/IL2Rg(null) mice. PLoS One 2013;8:e64384.

Carlsten M, Childs RW. Genetic Manipulation of NK Cells for Cancer Immunotherapy: Techniques and Clinical Implications. Front Immunol 2015;6:266.

Chang YH, Connolly J, Shimasaki N, Mimura K, Kono K, Campana D. A chimeric receptor with NKG2D specificity enhances natural killer cell activation and killing of tumor cells. Cancer Res 2013;73:1777-86.

Childs RW, Carlsten M. Therapeutic approaches to enhance natural killer cell cytotoxicity against cancer: the force awakens. Nat Rev Drug Discov 2015, 487-498.

(Continued)

*Primary Examiner* — Elly-Gerald Stoica

(74) *Attorney, Agent, or Firm* — Meunier Carlin & Curfman LLC

(57) ABSTRACT

Disclosed are compositions and methods for directing NK cells to the bone marrow through the use of PM21 particles.

3 Claims, 12 Drawing Sheets

(56) References Cited

OTHER PUBLICATIONS

Davis ZB, Cooley SA, Cichocki F, Felices M, Wangen R, Luo X, et al. Adaptive Natural Killer Cell and Killer Cell Immunoglobulin-Like Receptor-Expressing T Cell Responses are Induced by Cytomegalovirus and Are Associated with Protection against Cytomegalovirus Reactivation after Allogeneic Donor Hematopoietic Cell Transplantation. Biol Blood Marrow Transplant 2015, 1653-1662.
Denman CJ, Senyukov VV, Somanchi SS, Phatarpekar PV, Kopp LM, Johnson JL, et al. Membrane-bound IL-21 promotes sustained ex vivo proliferation of human natural killer cells. PLoS One 2012;7:e30264.
Dijkers PF, Birkenkamp KU, Lam EW, Thomas NS, Lammers JW, Koenderman L, et al. FKHR-L1 can act as a critical effector of cell death induced by cytokine withdrawal: protein kinase B-enhanced cell survival through maintenance of mitochondrial integrity. J Cell Biol 2002;156:531-42.
Fehniger TA, Cooper MA, Nuovo GJ, Cella M, Facchetti F, Colonna M, et al. CD56bright natural killer cells are present in human lymph nodes and are activated by T cell-derived IL-2: a potential new link between adaptive and innate immunity. Blood 2003;101:3052-7.
Foley B, Cooley S, Verneris MR, Curtsinger J, Luo X, Waller EK, et al. Human cytomegalovirus (CMV)-induced memory-like NKG2C(+) NK cells are transplantable and expand in vivo in response to recipient CMV antigen. J Immunol 2012;189:5082-8.
Foley B, Cooley S, Verneris MR, Pitt M, Curtsinger J, Luo X, et al. Cytomegalovirus reactivation after allogeneic transplantation promotes a lasting increase in educated NKG2C+ natural killer cells with potent function. Blood 2012;119:2665-74.
Fujisaki H, Kakuda H, Shimasaki N, Imai C, Ma J, Lockey T, et al. Expansion of highly cytotoxic human natural killer cells for cancer cell therapy. Cancer Res 2009;69:4010-7.
Geller MA, Knorr DA, Hermanson DA, Pribyl L, Bendzick L, McCullar V, et al. Intraperitoneal delivery of human natural killer cells for treatment of ovarian cancer in a mouse xenograft model. Cytotherapy 2013;15:1297-306.
Gleason MK, Ross JA, Warlick ED, Lund TC, Verneris MR, Wiernik A, et al. CD16xCD33 bispecific killer cell engager (BiKE) activates NK cells against primary MDS and MDSC CD33+ targets. Blood 2014;123:3016-26.
Glienke W, Esser R, Priesner C, Suerth JD, Schambach A, Wels WS, et al. Advantages and applications of CAR-expressing natural killer cells. Front Pharmacol 2015;6:21.
Klingemann HG. Cellular therapy of cancer with natural killer cells—where do we stand? Cytotherapy 2013;15:1185-94.
Knorr DA, Bachanova V, Verneris MR, Miller JS. Clinical utility of natural killer cells in cancer therapy and transplantation. Semin Immunol 2014;26:161-72.
Kohrt HE, Thielens A, Marabelle A, Sagiv-Barfi I, Sola C, Chanuc F, et al. Anti-KIR antibody enhancement of anti-lymphoma activity of natural killer cells as monotherapy and in combination with anti-CD20 antibodies. Blood 2014;123:678- 86.
Leclercq G, Debacker V, de Smedt M, Plum J. Differential effects of interleukin-15 and interleukin-2 on differentiation of bipotential T/natural killer progenitor cells. J Exp Med 1996;184:325-36.
Miller JS, Rooney CM, Curtsinger J, McElmurry R, McCullar V, Verneris MR, et al. Expansion and homing of adoptively transferred human natural killer cells in immunodeficient mice varies with product preparation and in vivo cytokine administration: implications for clinical therapy. Biol Blood Marrow Transplant 2014;20:1252-7.
Miller JS, Soignier Y, Panoskaltsis-Mortari A, McNearney SA, Yun GH, Fautsch SK, et al. Successful adoptive transfer and in vivo expansion of human haploidentical NK cells in patients with cancer. Blood 2005;105:3051-7.
Miller JS. Should natural killer cells be expanded in vivo or ex vivo to maximize their therapeutic potential? Cytotherapy 2009;11:259-60.
Nguyen S, Kuentz M, Vernant JP, Dhedin N, Bories D, Debre P, et al. Involvement of mature donor T cells in the NK cell reconstitution after haploidentical hematopoietic stem-cell transplantation. Leukemia 2008;22:344-52.
Oyer JL, Igarashi RY, Kulikowski AR, Colosimo DA, Solh MM, Zakari A, et al. Generation of highly cytotoxic natural killer cells for treatment of acute myelogenous leukemia using a feeder-free, particle-based approach. Biol Blood Marrow Transplant 2015;21:632-9.
Park KU, Jin P, Sabatino M, Feng J, Civini S, Khuu H, et al. Gene expression analysis of ex vivo expanded and freshly isolated NK cells from cancer patients. J Immunother 2010;33:945-55.
Phan TG, Long GV, Scolyer RA. Checkpoint inhibitors for cancer immunotherapy. Multiple checkpoints on the long road towards cancer immunotherapy. Immunol Cell Biol 2015;93:323-5.
Rodella L, Zamai L, Rezzani R, Artico M, Peri G, Falconi M, et al. Interleukin 2 and interleukin 15 differentially predispose natural killer cells to apoptosis mediated by endothelial and tumour cells. Br J Haematol 2001;115:442-50.
Rolle A, Pollmann J, Ewen EM, Le VT, Halenius A, Hengel H, et al. IL-12-producing monocytes and HLA-E control HCMV-driven NKG2C+ NK cell expansion. J Clin Invest 2014;124:5305-16.
Romagne F, Andre P, Spee P, Zahn S, Anfossi N, Gauthier L, et al. Preclinical characterization of 1-7F9, a novel human anti-KIR receptor therapeutic antibody that augments natural killer-mediated killing of tumor cells. Blood 2009;114:2667-77.
Romee R, Foley B, Lenvik T, Wang Y, Zhang B, Ankarlo D, et al. NK cell CD16 surface expression and function is regulated by a disintegrin and metalloprotease-17 (ADAM17). Blood 2013;121:3599-608.
Ross ME, Caligiuri MA. Cytokine-induced apoptosis of human natural killer cells identifies a novel mechanism to regulate the innate immune response. Blood 1997;89:910-8.
Sarkar S, van Gelder M, Noort W, Xu Y, Rouschop KM, Groen R, et al. Optimal selection of natural killer cells to kill myeloma: the role of HLA-E and NKG2A. Cancer Immunol Immunother 2015.
Shimasaki N, Fujisaki H, Cho D, Masselli M, Lockey T, Eldridge P, et al. A clinically adaptable method to enhance the cytotoxicity of natural killer cells against B-cell malignancies. Cytotherapy 2012;14:830-40.
Somanchi SS, Senyukov VV, Denman CJ, Lee DA. Expansion, purification, and functional assessment of human peripheral blood NK cells. J Vis Exp 2011, , e2540.
West WH, Tauer KW, Yannelli JR, Marshall GD, Orr DW, Thurman GB, et al. Constant-infusion recombinant interleukin-2 in adoptive immunotherapy of advanced cancer. N Engl J Med 1987;316:898-905.
Zhu EF, Gai SA, Opel CF, Kwan BH, Surana R, Mihm MC, et al. Synergistic innate and adaptive immune response to combination immunotherapy with anti-tumor antigen antibodies and extended serum half-life IL-2. Cancer Cell 2015;27:489-501.
International Preliminary Report on Patentability issued for Application No. PCT/US2018/020187, dated Sep. 12, 2019.
Oyer, Jeremiah L., et al. Natural killer cells stimulated with PM21 particles expand and biodistribute in vivo: clinical implications for cancer treatment. Cytotherapy 18.5 (2016): 653-663.
Bogova V.S. et al., Multiple secondary tumors. A Clinical event of progression of Acute Myeloblastic Leukemia and Myelogenous sarcomata among the patients with Hodgkin's lymphoma, Bulletin of medical on-line conferences, vol. 4, No. 5, 2014, p. 526.
Baykov V.V. et al., Beta-herpes-virus infections among patients with dermatic form of acute graft-versus-host disease, Infectology journal, 2015, 7(2), p. 65-69, https://doi.org/10.22625/2072-6732-2015-7-2-65-69.
Second Office Action issued in corresponding RU Application No. 2019129841, dated Dec. 29, 2021, 6 pages.
Pascale, Andre, "Modification of P-selectin glycoprotein ligand-1 with a natural killer cell-restricted sulfated lactosamine creates an alternate ligand for L-selectin", PNAS, 2000, vol. 97, No. 7, pp. 3400-3405.
Supplementary European Search Report for Application No. 18761720 dated Jul. 28, 2020.

(56) References Cited

OTHER PUBLICATIONS

Oyer et al., In Vivo Expansion of NK Cells Stimulated with PM21 Particles Under Ultralow IL-2, Biology of Blood and Marrow Transplantation, vol. 21, No. 2, Feb. 2015.
Written Opinion for Singaporean Application No. 11201907917X dated Nov. 25, 2021.
Chinese Office Action issued for Application No. 201880014665.4, dated May 8, 2023.

* cited by examiner

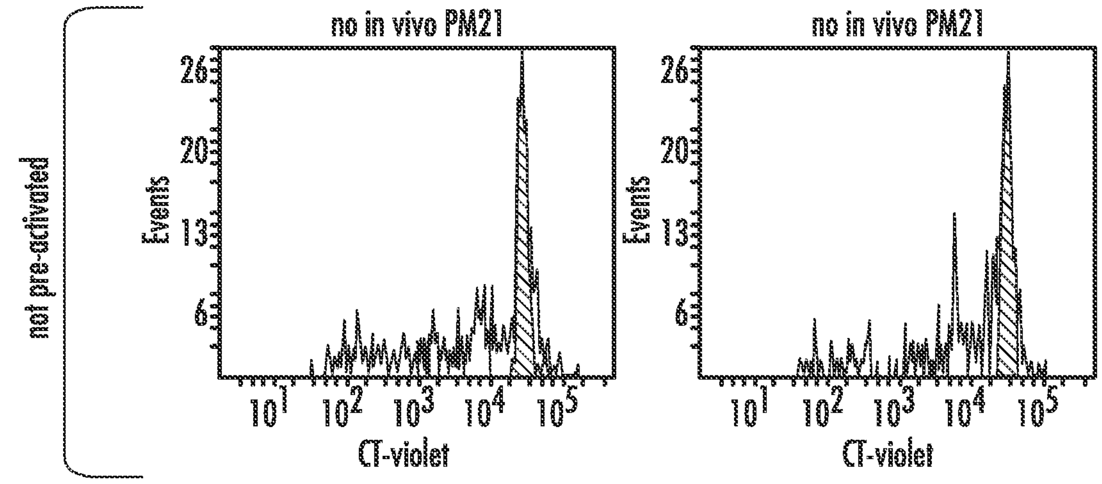
FIG. 3A
FIG. 3B
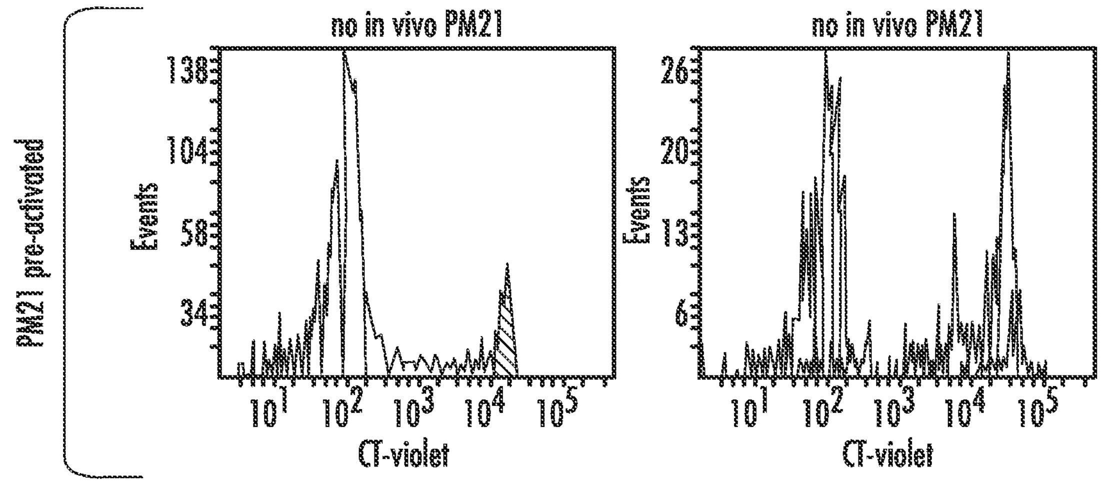
FIG. 3C
FIG. 3D

HECA staining of NK cells cultured with various conditions

HECA staining retained on NK cells after 3 days of rest without any stimulation following 10 day expansion

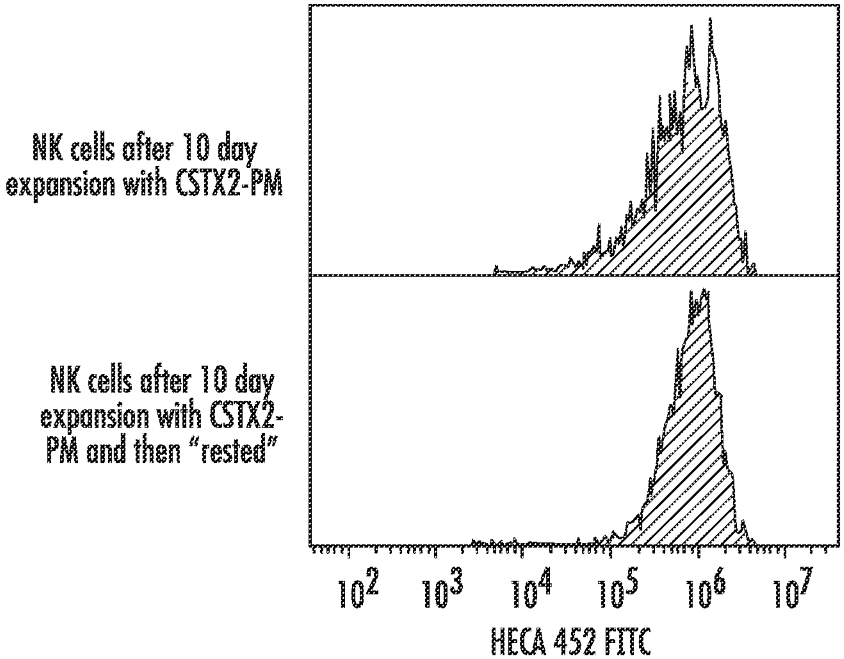

NK cells were cultured for 10 days with CSTX2-PM21-particles (top) and then "rested" in culture for 3 days after removing PM21-particles (bottom). NK cells were probed with FITC conjugated HECA452 mAb that detects fucosylated form of SLex. Cells from culture were stained with HECA452-FITC and analyzed by flow cytometry by gating on CD56+CD3-. (CSTX2 = CytoSen's K562.mb21.41bbl;FC=feeder cells; PM21=plasma membrane particles prepared from CSTX2)

FIG. 11

HECA staining of pre- and post- freeze thaw after 14 day expansion with CSTX2-PM21

Initial NK cells without expansion

After 14 day expansion with CSTX2-PM21-particles

Post-thawing after cryopreservation

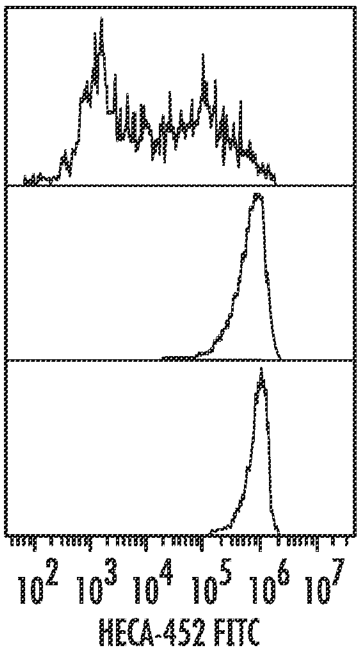

NK cells were isolated from PBMCs (top), then cultered for 10 days with CSTX2-PM21-particles (middle), and then cryopreserved and thawed (bottom).NK cells were probed with FITC conjugated HECA 452 mAb that detects fucosylated form of SLex. Cells from culture were stained with HECA452-FITC and analyzed by flow cytometry by gating on CD56+CD3-. (CSTX2 = CytoSen's K562.mb21.41bbl;FC=feeder cells; PM21=plasma membrane particles prepared from CSTX2)

*FIG. 12*

METHOD OF TREATING VIRAL INFECTIONS WITH NK CELLS TREATED WITH PM21 PARTICLES

This application claims the benefit of U.S. Provisional Application No. 62/464,747, filed on Feb. 28, 2017, and which is incorporated herein by reference in its entirety.

I. BACKGROUND

Adoptive natural killer (NK) cell therapy is a promising novel intervention for oncology including for bone marrow malignancies. Therefore, the efficiency for trafficking of the NK cells to be used adoptively is of high importance. What are needed are methods that can efficiently traffic NK cells to the bone marrow.

II. SUMMARY

Disclosed are methods and compositions related to trafficking NK cells to the bone marrow comprising contacting NK cells with PM21 particles and/or FC21 feeder cells. In one aspect, the methods can further comprise stimulating the NK cells with IL-2, IL-12, IL-18, and/or IL-18.

Also disclosed are methods of treating a bone marrow malignancy or bone marrow born malignancy and/or treating a viral infection (such as a bone marrow associated viral infection including a bone marrow tropic viral infection or viral infection that adversely effects the bone marrow) comprising contacting NK cells with PM21 particles and/or FC21 feeder cells and adoptively transferring NK cells to the subject. In some aspects, the contact of the PM21 particles and/or FC21 feeder cells with the NK cells can occur prior to transfer of the NK cells to a patient. In another aspect, the contact of the PM21 particles and/or FC21 feeder cells with the NK cells can occur in the patient.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows that PM-21 particles expand cytotoxic NK cells efficiently and selectively. Peripheral blood mononuclear cells (PBMCs) were isolated from leukocyte source and seeded at $0.1\times10^6$ NK cells/mL in SCGM supplemented with 10% FBS, 2 mM Glutamax and 50 U/mL IL-2. PBMCs were stimulated with PM15 (□, black) or PM21 (○, blue) particles at 200 μg/mL for 27 days, the cell content was tested every 2-3 days and shown are relative fold of NK cell expansion (A) and the percentage of suspension cells (B). PM21-particles (825±188 fold, N=13, 4 donors) (blue) are more efficient for NK cell expansion compared to PM15-particles (425±71, N=35, 9 donors) (black) based on cumulative analysis of day 14 data for NK cell expansion (C). PBMCs isolated from three AML patients in remission were cultured for 14 days with PM21-particles (200 μg/mL), seeded at $0.5\times10^6$ NK cells/mL in SCGM with 10% FBS, 2 mM Glutamax, 50 U/mL IL-2. Shown are fold of NK cell expansion from the primary PBMCs (D) and lymphocyte content (E) ($CD56^+CD3^-$ NK cells (●, red), $CD56^-CD3^+$ T cells (■, blue) and $CD56^+CD3^+$ NKT cells (▲, black)). PBMCs from patient F021 were cultured for 16 days as previously above and autologous cytotoxicity toward AML tumors from the same patient was analyzed (F). Expanded PM21-NK cells labeled with TFL4, and were co-incubated (2 hours) at indicated E:T ratios with AML cells from the same patient during active disease, and analyzed by flow cytometry. The amount of spontaneous dead target cells was determined using a "Target Alone" control. Each data point was determined in duplicate.

FIG. 2 shows that Pre-activation of unselected PBMCs with PM21-particles induces in vivo NK cell expansion. NSG mice were injected i.p. with $2\times10^6$ cells of either un-activated PBMCs (A and B) or PBMCs pre-activated ex vivo with PM21-particles and 100 U/mL IL-2 for two days (PM21-PBMCs) (C and D). Mice in all groups received 1,000 U of IL-2, i.p., thrice weekly. Groups of mice were also injected with 400 μg of PM21-particles, i.p., twice weekly (B and D). Peripheral blood was drawn by sequential cheek bleeds and analyzed by flow cytometry for $hCD45^+$ human lymphocytes twice weekly starting on day 6. NK, T and B cell amounts were determined based on staining for hCD3, hCD56, hCD19. The left plots in each experimental group shows concentration of hNK cells per μL of PB. The right plots shows the percentage of hNK cells (○, red) and T cells (∇, black) as fraction of total $hCD45^+$ cells.

FIG. 3 shows that Proliferation analysis evidences in vivo NK cell expansion from PM21-PBMCs. PBMCs freshly thawed or pre-activated with PM21-particles and 100 U/mL IL-2 for two days (PM21-PBMCs) were labeled with Cell Trace (CT) Violet. $2\times10^6$ of un-activated PBMCs (A and B) or PM21-PBMCs (C and D) were injected i.p. to NSG mice. Mice in all groups received 1,000 U IL-2, i.p., thrice weekly. Two of the groups of mice were also injected with 400 μg of PM21-particles, i.p., twice weekly (B and D). Two mice from each group were euthanized on day 6 and the peritoneal wash was analyzed by flow cytometry for CT Violet fluorescence of $hCD45^+$, $hCD3^-$, $hCD56^+$ NK cells. Histograms of the CT Violet fluorescence was analyzed through curve fitting using the Proliferation analysis suite within FlowLogic.

FIG. 4 shows that In vivo application of PM21 allows increase of NK cells in peripheral blood. PBMCs were pre-activated ex vivo with PM21-particles and 100 U/mL IL-2 for 2 days. PM21-PBMCs in the amount containing $0.2\times10^6$ of viable NK cells were injected i.p. to NSG mice. Mice in all groups received 1,000 U of IL-2, i.p., thrice weekly. Mice were also injected with 0 (A), 400 (B), 800 (C), 1,600 μg (D) of PM21-particles, i.p., twice weekly. Peripheral blood was analyzed by flow cytometry for $hCD45^+$ lymphocytes twice weekly starting on day 5 and hNK, hT and hB cell amounts were determined based on staining for hCD3, hCD56, hCD19. The left plots in each experimental group shows concentration of hNK cells per μL of PB. The right plots shows the percentage of hNK cells (○, red) and T cells (∇, black) as fraction of total $hCD45^+$ cells. Analysis of PB samples from day 12 after initial injection i.p. of PM21-PBMCs shows a dose dependent increase of PB hNK cells with respect to in vivo PM21-particle dose (E left) while no significant dose dependent increase in total $CD3^+$ T cells was observed (E right).

FIG. 5 shows that In vivo expanded NK cells biodistribute to key physiological sites and the NK cell biodistribution is increased with in vivo application of PM21-particles. NK cells ($0.2\times10^6$ cells) as part of PM21-PBMCs, pre-activated ex vivo with PM21-particles and 100 U/mL IL-2 for 2 days, were injected i.p. to NSG mice. Mice in all groups received 1,000 U of IL-2, i.p., thrice weekly. Mice were also injected with 0 or 800 μg of PM21-particles, i.p., twice weekly. Mice were sacrificed 16 days after initial injection i.p. of PM21-PBMCs. On day of euthanasia bone marrow (femur), spleen, lung, brain and liver were collected, organs were perfused while femur was washed to recover cells. Cells were stained with antibodies against hCD3, hCD45, hCD56, hCD19 for flow cytometry analysis. Data for bone marrow, spleen, brain, lung and liver (left to right) are shown with the amount of $hCD45^{+}hCD56^{+}hCD3^{-}$ NK cells (top plots for each organ) and percentages for $hCD45^{+}hCD56^{+}hCD3^{-}$ NK cells (○, red), $hCD45^{+}hCD3^{+}$ T cells (□, blue) and $hCD45^{+}$, $hCD56^{-}hCD3^{-}$ other lymphocytes (Δ, black) are shown (bottom plots for each organ). The thick bar for each represents the mean.

FIG. 6 shows that In vivo NK cells expansions from different donor sources are consistent. The consistency of PM21-particle stimulated in vivo NK cell expansion was tested using three different PBMCs obtained from healthy donors. The PBMCs were pre-activated ex vivo for 2 days with PM21-particles and 100 U/mL IL-2 for 2 days (PM21-PBMCs) and were injected i.p. to NSG mice. Mice in all groups received 1,000 U of IL-2, i.p., thrice weekly. Peripheral blood was analyzed by flow cytometry for $hCD45^{+}$ lymphocytes twice weekly starting on day 5 and hNK, hT and hB cell amounts were determined based on staining for hCD3, hCD56, hCD19. Both the concentration of hNK cells in blood 12 days after i.p. PBMC injection (A) and the amount of NK cells collected in a wash of the abdominal cavity 14 days after i.p. PBMC injection (C) were similar between the different groups injected with different NK cell sources (p=0.84 for PB and p=0.69). The corresponding cell content of hNK cells (○, red), hT cells (□, blue) and other $hCD45^{+}$ cells (Δ, black) were also consistent between the groups injected with different PBMC sources in the peripheral blood (B) and in the abdomen (D). The thick bar for each represents the mean.

FIG. 11 shows HECA-452 staining of NK cells after three days of rest following 10 days of stimulation.

FIG. 12 shows HECA-452 staining of pre- and post-freeze thaw following 14 days expansion of PM21 particles.

Figure 1A:
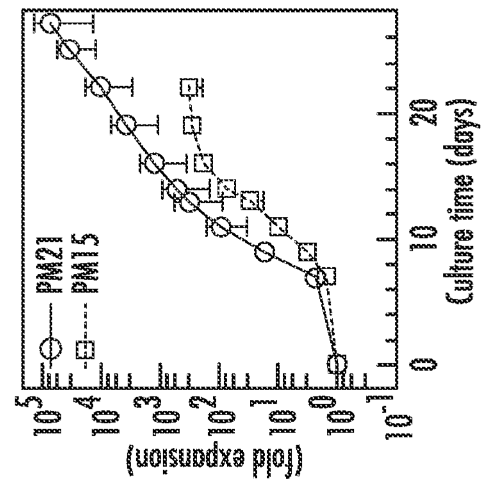
Figure 1B:
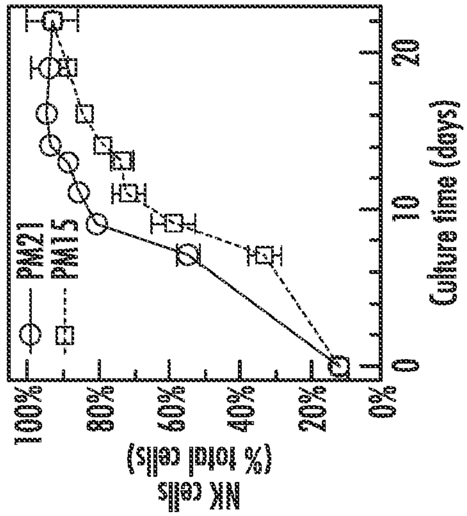

FIG. 13 shows that STAT3 is involved in IL-21 mediated modulation of FUT7 gene expression in human NK cells. (A) ChIP-seq was performed on IL-21 stimulated naïve and expanded human NK cells with antibodies against STAT3. The arrow indicates transcription directionality. Scales are constant for the gene and islands; (B) RNA-seq reveals the differential regulation of FUT7 gene expression in response to IL-21 stimulation; (C) IL-21 enhances STAT3 binding to FUT7 gene in expanded NK cells, and (D) IL-21 upregulates FUT7 gene expression in expanded NK cells.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

B. Methods of Using the Compositions

Adoptive natural killer (NK) cell therapy is a promising novel intervention for oncology including for bone marrow malignancies and bone marrow bom malignancies; and including veterinary applications for such. In another aspect, adoptive NK cells can be therapeutically used for treatment of marrow resident viruses, including for example. parvoviruses that cause aplastic anemia. Therefore, the efficiency for trafficking of the NK cells to be used adoptively is of high importance. In particular, how to drive transferred cells into the bone marrow where they can be effective as a treatment is of critical importance.

Among the determinants of marrow homing are ligands for selectin binding. For binding L-Selectin, a key determinant is the fucosylation state of sialyl Lewis x (sLex)

carbohydrate chain attached to P-selectin glycoprotein ligand-1 (PSGL-1). In one aspect, it is disclosed herein contemplated that stimulation of NK cells with PM21 particles and/or FC21 feeder cells prepared from K562 cells transformed to express engineered membrane bound form of IL-21 and/or 41bbl (K562.mb21.41bbl) induces efficient specific expansion of NK cells and induces full fucosylation of sLex.

Accordingly in one aspect, disclosed herein are methods related to trafficking NK cells to the bone marrow and methods of treating a bone marrow malignancy or bone marrow born malignancy comprising contacting NK cells with PM21 particles and/or FC21 feeder cells and adoptively transferring the NK cells to a patient in need thereof. In one aspect, the methods can further comprise stimulating the NK cells with IL-2, IL-12, IL-15 IL-18, IL-21 either ex vivo or in vivo (in the patient).

In some aspects, the contact of the PM21 particles and/or FC21 feeder cells with the NK cells can occur prior to transfer of the NK cells to a patient. In another aspect, the contact of the PM21 particles and/or FC21 feeder cells with the NK cells can occur in the patient.

In one aspect, it is understood and herein contemplated that the efficacy of NK cell immunotherapy is dependent on the dose of NK cells administered to the patient or reached after infusion through in vivo expansion. Currently available techniques are limited by their inability to achieve the level of NK cell expansion required to achieve a therapeutic effect in a patient. The lack of a simpler clinical expansion protocol is a major barrier to the progress and wide dissemination of NK cell-based immunotherapy. Current ex vivo expansion protocols use a combination of high dose cytokines with activating ligands expressed on leukemia-derived feeder/stimulator cell lines, posing a significant disadvantage for transfer to clinical settings in most centers and are not amenable for direct in vivo expansion. The use of particle technology, including exosomes, described herein eliminates the need for stimulator cells, thus simplifying the methodology and allowing ex vivo expansion for adoptive therapy or applied in vivo for selective in vivo expansion. Accordingly, and in one aspect, disclosed herein are methods for treating bone marrow malignancies and bone marrow born malignancies through the adoptive transfer of NK cells and/or methods trafficking NK cells to the bone marrow comprising contacting NK cells with one or more vesicles comprising an NK cell effector agent. In one aspect, also disclosed are methods of treating bone marrow malignancies, bone marrow born malignancies, and or viral infections (including viruses with a bone marrow tropism) further comprising preactivating or activating in vivo NK cells by contacting at least one NK cell with at least one or more stimulatory cytokines. Thus, in one aspect, NK cells expanded ex vivo by PM21 particles and/or FC21 feeder cells, or with direct in vivo stimulation with PM21 or FC21 feeder cells can be used to treat marrow resident viral conditions or syndromes (e.g. parvovirus) that cause aplastic anemia.

The disclosed methods accomplish preactivation or activation of NK cells by contacting at least on NK cell with at least one or more stimulatory cytokines (for example IL-2, IL-12, IL-15, IL-21 and/or IL-18). Thus, in one aspect, disclosed herein are methods of treating bone marrow malignancies and bone marrow born malignancies through the adoptive transfer of NK cells and/or methods trafficking NK cells to the bone marrow comprising preactivating NK cells by contacting one or more NK cells with one or more stimulatory cytokines is selected from the group comprising IL-2, IL-12, IL-21, IL-15, and/or IL-18, or any combination thereof, including contacting one or more NK cells with 2 or 3 stimulatory cytokines. For example, specifically disclosed herein are methods wherein the preactivation or activation step comprises contact NK cells with IL-2; IL-12; Il-15, IL-18, IL-12 and IL-15; IL-12 and IL-18; IL-15 and IL-18; or IL-12, IL-15, and IL-18. In one aspect, the disclosed methods of treating bone marrow malignancies and bone marrow born malignancies through the adoptive transfer of NK cells and/or methods trafficking NK cells to the bone marrow can further comprise contacting the NK cell with one or more cytokines selected from the group consisting of 4-1BBL, IL-2, IL-21, MICA/B, ULBP2, ICAM-1, 2B4, BCM1/SLAMF2, CD155, CD112, CCR7, DAP12, Notch ligands and/or DAP10 in soluble form or in the form PM21 particles or FC21 feeder cells.

It is understood and herein contemplated that the duration of preactivation or activation (i.e., the duration of contact between the NK cells and the stimulatory cytokines (e.g., IL-2, IL-12, IL-15, IL-21 and/or IL-18) in soluble form or in the form PM21 particles or FC21 feeder cells can be for any length of time necessary to achieve the desired preactivation or activation of NK cells. For example, the contact can be as little as 1 minute or as much as 7 days (for example, culturing the NK cells in the presence of IL-2, IL-12, IL-15, IL-21 and/or IL-18 for 7 days). In one aspect, disclosed herein are methods of treating bone marrow malignancies and bone marrow born malignancies through the adoptive transfer of NK cells and/or methods trafficking NK cells to the bone marrow comprising preactivating or activating NK cells by contacting one or more NK cells with IL-2, IL-12, IL-15, and/or IL-18 for 5, 6, 7, 8, 9, 10, 11, 12, 13, 14, 15, 16, 17, 18, 19, 20, 21, 22, 23, 24, 36, or 48 hours. It is understood and herein contemplated that the half-life of a cytokine in culture may be less than the desired contact time. Accordingly, disclosed herein are methods wherein one or more NK cells are contacted with IL-2, IL-12, IL-15, and/or IL-18 every 1, 2, 3, 4, 5, 6, 7, 8, 9, 10, 11, or 12 hours within a contact period (for example, every 1, 2, 3, 4, 5, 6, 7, 8, 9, 10, 11, or 12 in a 24 hour contact period).

Through the use of plasma membrane (PM) particles, exosomes (EX), or feeder cells (FC) comprising one or more NK cell effector agents (i.e., stimulatory peptides, cytokines, and/or adhesion molecules) to contact and activate and/or expand NK cells many hurdles associated with cytokine toxicity are overcome. Examples of NK cell activating agents and stimulatory peptides include, but are not limited to, 41BBL, IL-2, IL-12, IL-21, IL-18, MICA, LFA-1, 2B4, BCM/SLAMF2, CCR7, Notch ligands and/or other homing inducing signaling molecules. Examples of cytokines include, but are not limited to, IL-2, IL-12, IL-21, and IL-18. Examples of adhesion molecules include, but are not limited to LFA-1, MICA, BCM/SLAMF2. For example, a plasma membrane (PM) particle, Feeder cells (FC), or exosomes (EX) prepared from feeder cells expressing membrane bound IL-21 (FC21 cells, PM21 particles, and EX21 exosomes, respectively). The membrane bound IL-21 expressing FC21 cells, PM21 particles, and EX21 exosomes can further comprise additional one or more activating agents, stimulatory peptides, cytokines, and/or adhesion molecules including, but not limited to 41BBL, IL-2, IL-12, IL-15, IL-18, MICA, LFA-1, 2B4, BCM/SLAMF2, CCR7 (for example, PM21 particle, EX21 exosome, or FC cell expressing 41BBL and membrane bound interleukin-21). Accordingly, in one aspect, disclosed herein are methods of treating bone marrow malignancies and bone marrow born malignancies through the adoptive transfer of NK cells and/or methods trafficking NK cells to the bone marrow comprising by contacting said cells with at least one vesicle comprising an NK cell effector agent; wherein the NK cell effector agent comprising vesicle is any combination of one or more of PM21 particle, EX21 particle, and/or FC21 feeder cells. For example, disclosed herein are methods of treating bone marrow malignancies and bone marrow born malignancies through the adoptive transfer of NK cells and/or methods trafficking NK cells to the bone marrow comprising, amongst other steps contacting said cells with at least one vesicle comprising an NK cell effector agent wherein the NK cell effector agent comprising vesicle comprises PM21 particles; EX21 exosomes; FC21 feeder cells; PM21 particles and EX21 exosomes; PM21 particles and FC21 feeder cells; EX21 exosomes and FC21 feeder cells; or PM21 particles, EX21 exosomes, and FC21 feeder cells.

In some aspects, effector agents of the PM21 particles, EX21 exosomes, or FC21 feeder cells comprise one or more stimulatory peptides coupled to a membrane-inserting peptide (for example, Fc, GPI, trans-membrane T-cell receptor, or pHLIP). A membrane-inserting peptide may be a molecule that promotes insertion into a membrane. Membrane-inserting peptides may comprise segments of CD4 or an IgG with affinity for a lipid bilayer. In addition, alternative membrane-inserting peptides may comprise human Fc, GPI, trans-membrane T-cell receptor, or pHLIP. The membrane self-inserting peptide may be any peptide known to insert into a cell membrane. Depending on the use of the membrane self-inserting peptide conjugate, certain membrane self-inserting peptides can be better choices than others. One of skill in the art would understand what membrane self-inserting peptide is ideal under different circumstances. For example, for in vivo use, pHLIP membrane self-inserting peptide may be suitable. pHLIP membrane self-inserting peptides insert into the membrane only under conditions of low pH. Therefore, pHLIP conjugates will not insert into cell membranes under normal physiological conditions. However, upon injection into a tumor environment, the pHLIP conjugate can insert into the cell membrane of tumor cells because the tumor environment is more acidic than normal physiological conditions. This insertion into the tumor environment allows for activation of NK cells in the area of the tumor. Using pHLIP thus prevents unwanted insertion into random cell membranes.

Membrane-inserting peptides may be coupled to one or more stimulatory peptides in a variety of ways and techniques for coupling peptides are well known in the art. A membrane-inserting peptide coupled to a stimulatory peptide can also be referred to as a membrane-inserting peptide conjugate. In some aspects, the one or more stimulatory peptides coupled to a membrane-inserting peptide may comprise a fusion protein encoded by recombinant DNA and such fusion-proteins may be produced in bacterial cells. In certain embodiments, fusion proteins may consist of one or more stimulatory peptides conjugated or coupled to a lipophilic molecule such as a hydrophobic peptide, GPI, or human Fc for anchoring into liposomes or cellular membranes. cDNA vectors for these fusion proteins may be ligated into an expression plasmid, which allows expression in bacterial (*E. coli*), insect, or mammalian cells. In certain embodiments, cDNA vectors may be FLAG- or HIS-tagged. Bacterial cells may be transfected using standard CaCl transfection methods, such as that described in Sambrook et al., Molecular Cloning: A Laboratory Manual. 2nd ed. Cold Spring Harbor Laboratory Press (1989). Bacterial cells may also be cultured in LB media and cells can be harvested and lysed using a French Press. Proteins of interest can be purified from lysates by affinity chromatography. Palmitate-conjugated protein A and purified Fc fusion proteins can be conjugated as described in the literature by mixing 1:2 (w/w) at 4 degrees C. The conjugates may then be directly injected intratumorally or may be incorporated into liposomes.

Types of coupling and methods for coupling are known to those skilled in the art. As used herein, term "couple" refers to the membrane self-inserting peptide being conjugated, connected, or otherwise linked to another molecular entity such as a peptide or protein. For example, membrane-inserting peptides coupled to stimulatory peptides can be fusion proteins wherein the membrane-inserting peptide is coupled to another protein via a disulfide bond. Coupling or conjugating may mean that there is a chemical linkage between the membrane self-inserting peptide and the NK cell effector agent.

In some aspects, one or more stimulatory peptides may be coupled to membrane self-inserting peptides or GPI anchors for in situ self-assembly. For example, 41-BBL and IL-21 may be coupled to a pHLIP peptide which inserts itself into cellular membranes under acidic conditions, thereby allowing the anchoring of the stimulatory ligands into cells in the proximity of tumor. The stimulatory peptides 41BBL, IL-2, IL-12, IL-21, BCM/SLAMF2, CCR7 and/or other homing receptors may be produced in bacterial cells or purchased from commercially available sources and cDNA vectors for these proteins may optionally be ligated into pTriEX expression plasmid which allows expression in bacterial (*E. coli*), insect, or mammalian cells. The cDNA vector may code for expression of FLAG- or HIS-tag. Bacterial cells can be transfected using standard CaCl transfection methods and may be cultured on LB media. Cells can be harvested and lysed using a French press and proteins of interest may then be purified from lysates by affinity chromatography.

In some embodiments, pHLIP may be prepared by solid-phase peptide synthesis using 9-fluorenylmethyloxycarbonyl chemistry and the product may be purified on a C18 column by reverse-phase chromatography. pHLIP may then be conjugated to stimulatory human protein ligands by incubating with a crosslinker, such as benzophenone-4-iodoacetamide. After several washes, the conjugated pHLIP protein may be resuspended in media (saline, for example) and injected intratumorally or intravenously. Based on evidence from prior literature and presented in experimental results, interaction of NK cells with stimulatory ligands such as IL-21 and 41-BBL on the surface of such modified tumor cells may stimulate in situ NK cell expansion and trigger their cytotoxic response toward a tumor. This type of stimulatory approach can be used for treatments of solid tumors such as ovarian cancer where NK stimulatory ligands that insert in situ into tumor cells under acidic pH can be injected into intraperitoneal space of patients with low dose IL-2 alone or together with NK cells. There is strong evidence that cytotoxic lymphocytes that express high levels of FCγIII R (CD16) such as NK cells are crucial for the efficacy of cancer therapy with therapeutic antibodies. Thus, this approach can also be used in combination with therapeutic antibodies.

It is understood and herein contemplated that the duration of contact between the NK cells and the NK cell effector agent comprising vesicle (i.e., PM21 particles, EX21 exosomes, and/or FC21 feeder cells) can be for any length of time necessary to achieve the desired expansion of memory NK cells. For example, the contact can be as little as 1 minute or as much as 60 days (for example, culturing the NK cells in the presence of PM21 particles, EX21 exosomes, and/or FC21 feeder cells for 7 days). In one aspect, the contact between the NK cells and the NK cell effector agent comprising vesicle can be between about 6 days and about 60 day, more preferably the contact can be between about 6 days and about 40 days. Also disclosed herein are methods of methods of treating bone marrow malignancies and bone marrow born malignancies through the adoptive transfer of NK cells and/or methods trafficking NK cells to the bone marrow comprising contacting NK cells with PM21 particles, EX21 exosomes, and/or FC21 feeder cells for 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 days. It is understood and herein contemplated that in some instances, multiple contact of the NK cells with PM21 particles, EX21 exosomes, and/or FC21 feeder cells may be desired and can be employed. For example, the NK cells can be contacted with the PM21 particles, EX21 exosomes, and/or FC21 feeder cells once every 1, 2, 3, 4, 5, 6, 7, 8, 9, 10, 11, 12, 18, 24 hrs, 2, 3, 4, 5, 6, 7, 8, 9, 0, 10, 11, 12, 13, 14, 15, 16, 17, 18, 19, 20, or 21 days. Accordingly, in one aspect, disclosed herein are methods of methods of treating bone marrow malignancies and bone marrow born malignancies through the adoptive transfer of NK cells and/or methods trafficking NK cells to the bone marrow NK cells comprising contacting the NK cells with PM21 particles, EX21 exosomes, and/or FC21 feeder cells more than one time, wherein the contact occurs every 1, 2, 3, 4, 5, 6, 7, 8, 9, 10, 11, 12, 18, 24 hrs, 2, 3, 4, 5, 6, 7, 8, 9, 0, 10, 11, 12, 13, 14, 15, 16, 17, 18, 19, 20, or 21 days.

In one aspect, the plasma membrane particles, feeder cells, or exosomes can be purified from feeder cells that stimulate NK cell. NK cell stimulating feeder cells for use in the claimed invention, for use in making the plasma membrane particles or exosomes, disclosed herein can be either irradiated autologous or allogeneic peripheral blood mononuclear cells (PBMCs) or nonirradiated autologous or PBMCs, RPM18866, HFWT, K562, SKOV3, or EBV-LCL cells including autologous or allogeneic peripheral blood mononuclear cells (PBMCs) or nonirradiated autologous or PBMCs, RPMI8866, HFWT, K562, SKOV3, or EBV-LCL cells transfected with membrane bound IL-21 and 41BBL. In some aspects, the NK cell feeder cells can be K562 cells transfected with membrane bound IL-21 and 41BBL.

The disclosed compositions can be used to treat any disease where uncontrolled cellular proliferation occurs such as cancers and, in particular, malignancies affecting or localizing in the bone marrow. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

The disclosed compositions can also be used to treat viral diseases associated with the bone marrow. As used herein, a viral disease is associated with the bone marrow refers to a viral disease in which the marrow harbors viruses (i.e., the virus infects (including chronic, acute, latent, and persistent infections) or otherwise has tropism for the bone marrow) or the bone marrow is adversely affected by the viruses, such as viruses that causes aplastic anemia, such as, for example parvovirus (in some cases, the disease or condition that adversely effects the bone marrow is a viral infection of the bone marrow). Thus, in one aspect, disclosed herein are methods of treating a viral infection in a subject, wherein the viral infection is associated with the bone marrow (for example, adversely affects the bone marrow) comprising contacting NK cells with PM21 particles and/or FC21 feeder cells and adoptively transferring NK cells to the subject with the viral infection. In one aspect, the virus can cause aplastic anemia and/or be a bone marrow tropic infection or viral infection that establishes a latent or chronic infection in the bone marrow. For example, the virus can include, but are not limited to dengue, hepatitis virus (including, but not limited to, Hepatitis A virus, Hepatitis B virus, Hepatitis C virus, Hepatitis D virus, Hepatitis E virus, and Hepatitis G virus), Epstein-Barr virus (also known as Human Herpes virus 4), cytomegalovirus (also known as Human Herpes virus 5), parvovirus (including but not limited to parvovirus B19), Lymphocytic choriomeningitis virus (LCMV), Human Immunodeficiency Virus (HIV), and respiratory syncytial virus (RSV).

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular PM21 particle or FC21 feeder cell is disclosed and discussed and a number of modifications that can be made to a number of molecules, specifically contemplated is each and every combination and permutation of the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The disclosed methods of treating bone marrow malignancies and bone marrow born malignancies through the adoptive transfer of NK cells and/or methods trafficking NK cells to the bone marrow utilize one or more cytokines (for example, IL-12, IL-15, and/or IL-18) in combination with a vesicle comprising an NK cell effector agent, such as, for example, PM21 particles, FC21 feeder cells, and/or EX21 exosomes. It is understood and herein contemplated that it would be advantageous to provide the components utilized in the disclosed methods in a package that would readily allow a person to perform the disclosed methods.

Thus, in one aspect, disclosed herein are kits for treating bone marrow malignancies and bone marrow born malignancies with NK cells comprising one or more cytokines (for example, IL-2, IL-12, IL-15 and/or IL-18) and one or more vesicles comprising an NK cell effector agent. In one aspect, the vesicle can be PM21 particles, EX21 exosomes, and/or FC21 feeder cells. For example, the disclosed kits can comprise IL-12 and PM21 particles; IL-15 and PM21 particles; IL-18 and PM21 particles; IL-12 and EX21 exosomes, IL-15 and EX21 exosomes; IL-18 and EX21 exosomes; IL-12 and FC21 feeder cells; IL-15 and FC21 feeder cells; IL-18 and FC21 feeder cells; IL-12, IL15, and PM21 particles; IL-12, IL-18, and PM21 particles; IL-15, IL-18, and PM21 particles; IL-12, IL-15, IL-18, and PM21 particles; IL-12, IL15, and EX21 exosomes; IL-12, IL-18, and EX21 exosomes; IL-15, IL-18, and EX21 exosomes; IL-12, IL-15, IL-18, and EX21 exosomes; IL-12, IL15, and FC21 feeder cells; IL-12, IL-18, and FC21 feeder cells; IL-15, IL-18, and FC21 feeder cells; IL-12, IL-15, IL-18, and FC21 feeder cells; IL-12, EX21 exosomes, and PM21 particles; IL-15, EX21 exosomes, and PM21 particles; IL-18, EX21 exosomes, and PM21 particles; IL-12, FC21 feeder cells, and PM21 particles; IL-15, FC21 feeder cells, and PM21 particles; IL-18, FC21 feeder cells, and PM21 particles; IL-12, FC21 feeder cells, and EX21 exosomes; IL-15, FC21 feeder cells, and EX21 exosomes; IL-18, FC21 feeder cells, and EX21 exosomes; IL-12, FC21 feeder cells, PM21 particles, and EX21 exosomes; IL-15, FC21 feeder cells, PM21 particles, and EX21 exosomes; IL-18, FC21 feeder cells, PM21 particles, and EX21 exosomes; IL-12, IL15, EX21 exosomes, and PM21 particles; IL-12, IL-18, EX21 exosomes, and PM21 particles; IL-15, IL-18, EX21 exosomes, and PM21 particles; IL-12, IL-15, IL-18, EX21 exosomes, and PM21 particles; IL-12, IL15, FC21 feeder cells, and PM21 particles; IL-12, IL-18, FC21 feeder cells, and PM21 particles; IL-15, IL-18, FC21 feeder cells, and PM21 particles; IL-12, IL-15, IL-18, FC21 feeder cells, and PM21 particles; IL-12, IL15, EX21 exosomes, and FC21 feeder cells; IL-12, IL-18, EX21 exosomes, and FC21 feeder cells; IL-15, IL-18, EX21 exosomes, and FC21 feeder cells; IL-12, IL-15, IL-18, EX21 exosomes, and FC21 feeder cells; IL-12, EX21 exosomes, FC21 feeder cells, and PM21 particles; IL-15, EX21 exosomes, FC21 feeder cells, and PM21 particles; IL-18, EX21 exosomes, FC21 feeder cells, and PM21 particles; IL-12, IL15, EX21 exosomes, FC21 feeder cells, and PM21 particles; IL-12, IL-18, EX21 exosomes, FC21 feeder cells, and PM21 particles; IL-15, IL-18, EX21 exosomes, FC21 feeder cells, and PM21 particles; or IL-12, IL-15, IL-18, EX21 exosomes, FC21 feeder cells, and PM21 particles.

It is understood and herein contemplated that the NK cell effector agents comprised in the vesicles (e.g., PM21 particles, EX21 exosomes, and/or FC21 feeder cells) can be selected from the group of NK cell effector agents consisting of 4-1BBL, IL-2, IL-21, MICA/B, ULBP2, ICAM-1, 2B4, BCM1/SLAMF2, CD155, CD112, CCR7, DAP12, Notch ligands and DAP10.

It is understood and herein contemplated that the disclosed kits or devices can comprise cytokines in addition to IL-12, IL-15, and/or IL-18. Accordingly, in one aspect are kits for methods of treating bone marrow malignancies and bone marrow born malignancies through the adoptive transfer of NK cells and/or methods trafficking NK cells to the bone marrow further comprising 4-1BBL, IL-2, IL-12, IL-18, IL-21, MICA/B, ULBP2, ICAM-1, 2B4, BCM1/SLAMF2, CD155, CD112, CCR7, DAP12, and DAP10.

In one aspect, it is contemplated herein that the disclosed kits or devices can be used with NK cells obtained from a donor source including NK cells obtained from an unselected population of peripheral blood mononuclear cells. In some instances the donor source for the NK cells being used in the disclosed kits for treating bone marrow malignancies and bone marrow born malignancies can also be the recipient for the NK cells. Accordingly, the NK cells can be from an autologous source. In other instances the donor source for the NK cells can be a haploidentical or allogeneic donor source.

It is further contemplated herein that there are instances where it would be beneficial to provide NK cells in the kit or device. Accordingly in one aspect, disclosed herein are kits for treating a bone marrow malignancy further comprising NK cells or an NK cell line.

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J Cancer,* 60:275-281, (1989); Bagshawe, et al., *Br. J Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, P A 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

D. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: PM21-Particles Stimulate In Vivo NK Cell Expansion

Natural killer (NK) cells are a component of the innate immune system, identified by being $CD56^{+}CD3^{-}$, and can naturally recognize and lyse cells that are virally compromised or are malignant. Cell therapy with NK cells is promising as a cancer treatment and multiple clinical trials have been conducted and are currently underway for treatment of various cancers (AML, lymphomas, breast, ovarian, neuroblastoma, non-small cell lung carcinomas). For effective anti-cancer therapy with NK cells, three general aspects must be considered: 1) a large enough dose of NK cells must be delivered; 2) NK cells must be highly cytotoxic; and 3) NK cells must reach, possibly localize at the site of disease, persist and specifically target tumor cells.

For clinical efficacy in an AML setting, Miller and coworkers have recommended attaining a dose that would provide at least 100 NK cells per μL of peripheral blood (PB) at two weeks post infusion. In some examples where treatment with adoptive NK cell therapy was efficacious, over 1,000 NK cells per μL of PB were observed. These observations highlight the importance of proficient NK cell expansion methods for delivery of a sufficient dose for overall treatment efficacy.

Currently, there are broadly three different clinically used strategies for NK cell expansion for adoptive cell therapy. First, in vivo expansion with cytokines such as IL-15 and IL-2, combined with host lymphodepletion/irradiation, can stimulate in vivo expansion from the relatively low amount of injected donor NK cells. Second, ex vivo methods with cytokines, mainly using IL-2 and IL-15, can activate NK cells, although expansion is relatively low and variable. Also, NK cells activated ex vivo with cytokines undergo cytokine withdrawal after infusion and the NK cells undergo apoptosis. Third, feeder cell methods for ex vivo NK cell expansion use co-cultures with other cells that are stimulatory. Feeder cell methods for NK cell stimulation include Epstein-Barr virus-LCLs, or engineered tumor cells. Coculture with K562 CML cells expressing membrane bound IL-15 (mb15) and 4-1BB ligand (41BBL) (K562-mb15-41BBL) are able to expand NK cells several hundred fold in about two weeks, but the NK cells expanded by this method experience senescence. In addition, NK cells activated with IL-15 lose surface CD16 by proteolytic activity of ADAM17. Rather K562 cells expressing mb21, instead of mb15, significantly improves NK cell expansion while avoiding telomere shortening and consequent NK cell senescence. Expansion of NK cells with the K562-mb21-41BBL is very efficient and a mean 48,000-fold expansion with >85% enrichment is typically achieved in three weeks. All of these methods are actively being investigated in clinical trials.

While NK cell expansion methods have improved, there are still disadvantages and challenges. High, toxic dose of IL-2 is required regardless of expansion method for survival of the infused NK cells, although the persistence of the NK cells has been limited. While ex vivo methods with feeder cells have been effective for expansion to generate large amounts of NK cells, concerns have been raised that long term ex vivo culturing of NK cells causes loss of ability to home to the site of disease such as bone marrow. Thus, there has been a debate about the overall benefits of in vivo vs. ex vivo expansion. An optimal NK cell expansion procedure would be a method which has the proliferation capability of an ex vivo feeder cell based method, but could be performed either ex vivo or in vivo.

A novel PM21 particle based method for rapid and selective expansion of cytotoxic NK cells starting with PB mononuclear cells (PBMCs). The particles corresponding to closed plasma membrane vesicles were prepared from plasma membrane of K562-mb15-41BBL cells (PM15-particles) and allowed selective NK cell expansion of 250-fold in 14 days and 1,265-fold after 17 days, which is comparable to the expansion efficiency using K562-mb15-41BBL feeder cells in co-culture. PM15-particle activated NK cells, similar to feeder cell expanded NK cells, were highly cytotoxic towards CML and AML cells ex vivo. Importantly, these particles offer many advantages over the feeder cell methods. First, they can be prepared in advance, tested and stored for more than a year, and can be used as an "off-the-shelf reagent" without being constrained to a single GMP facility, which greatly simplifies the clinical logistics of adoptive NK cell therapy. Second, use of the PM-particles, instead of feeder cells to stimulate NK cells, eliminates steps needed for safety measures when using tumor-derived feeder cell such as feeder cell irradiation and testing their presence and proliferation in the final product. Third, tumor-derived feeder cells cannot be injected as an adjuvant therapy whereas the PM-particles can be injectable to stimulate in vivo expansion of NK cells. The advantages offered by the PM-particle based method for NK cell expansion allows for significant clinical benefits.

Here in this work, the efficacy of PM-particles prepared from K562-mb21-41BBL was tested for in vivo expansion of adoptively transferred NK cells, pre-activated with a relatively short and simple procedure that can be easily implemented in a clinical setting. The method overcomes the shortcomings of previous studies with i.v. infusion of adoptive NK cells that only allowed very minimal in vivo NK cell expansion and limited persistence. For the current study, efficacy is shown for PM21-particle stimulated ex vivo and in vivo expansion of NK cells from unselected PBMCs injected into the peritoneal cavity, which is intended to serve as an in situ site for incubation and stimulation by PM21-particles. This method is expected to be useful for the in vivo expansion of NK cells at therapeutically relevant amounts and presents means to make NK cell-mediated immunotherapy more widely accessible to patients.

a) Materials and Methods (1) Human Samples

Primary leukemia blasts were obtained from patients, who signed an IRB-approved informed consent, during active disease and comparable PB was collected from these patients during remission. Leukocyte source (One Blood, Orlando, FL) or fresh blood collected from healthy volunteers who signed and IRB approved informed consent were used as healthy samples. PBMCs were isolated using Ficoll-Paque (GE Healthcare, Pittsburgh, PA). All samples were de-identified and viably cryopreserved.

(2) Reagents and Cell Lines

K562 cell line was obtained from ATCC (Manassas, VA). Annexin-V FITC kit for cytotoxicity assays and Enumeration Flow-Count beads purchased from Beckman Coulter (Miami, FL). The following dye conjugated antibodies were used for phenotyping: CD16-FITC, NKG2A-PE, NKp46-PE, CD3-APC (Beckman Coulter); CD4-APC-Cy7, CD8-PE, CD56-BV421, CD94-APC (BD Biosciences); CD3-Alexa488, NKG2D-APC, CD62L-PE-Cy7, CD45-eFluor450, CD45-APC (eBiosciences); CD56-PE, KIR2D-APC (Miltenyi); NKG2C-PE NKp44-APC, TRAIL-PE (R&D Systems).

(3) Preparation and Characterization of Plasma Membrane Particles

PM-particles were prepared from K562-mb21-41BBL cells. Cells were grown in RPMI-1640 media supplemented with 5% fetal bovine serum. Cells were harvested by centrifugation (1,000×g, 10 minutes), washed with DPBS containing 2 mM EDTA. Cells were re-suspended in lysis buffer containing 50 mM HEPES, pH 7.4, 150 mM NaCl, 2 mM $MgCl_2$ and AEBSF, Aprotinin, Leupeptin and Pepstatin A. Cells were disrupted by nitrogen cavitation at 300 psi for 30 minutes at 4° C. (Parr Instruments, Moline, IL). Cell lysate was centrifuged (1,000×g, 10 minutes) and the supernatant was then centrifuged (100,000×g) to pellet the crude cell membranes. The crude membranes were further purified by sucrose gradient centrifugation and the fraction that corresponds to closed plasma membrane vesicles was collected. All procedures were performed using aseptic techniques and sterility of the product was tested in culture. PM-particle preparations were quantified by protein concentration by BCA assay and specified as g of membrane protein/mL. Presence of IL-21 and 41BBL on PM-particles was confirmed by ELISA and Western Blot.

(4) Ex Vivo NK Cell Expansion from PBMCs

NK cells from PBMCs were expanded using PM21-particles. Briefly, PBMCs were seeded at $0.1\times10^6$ NK cells/mL in SCGM (CellGenix, Portsmouth, NH) supplemented with 10% FBS, 2 mM Glutamax, 100 U/mL IL-2 (Peprotech, Rocky Hill, NJ) and 200 μg/mL PM21-particles. Media with supplements was replaced routinely every 2-3 days after day 5.

(5) Autologous Patient NK Cell Cytotoxicity Assays

Cytotoxicity assays of patient derived NK cells against autologous AML tumor cells was assayed with Annexin V (BD Bioscience). NK cells expanded for 16 days (NK cell content>90%) were stained with TFL4 dye. Target tumor cells were co-cultured at $0.5\times10^6$ $CD34^+$ cells/mL with NK cells at E:T ratios of 1:1, 2:1, 5:1, and 10:1 for 2 hours in 37° C., 5% $CO_2$ atmosphere. The cells were then centrifuged and resuspended in Annexin V labelling buffer containing Annexin V-FITC, anti-CD34-PE, and anti-CD56-PC7 and incubated for 15 minutes at 4° C. The labeled cells were diluted to 250 μL and analyzed by flow cytometry on an Accuri instrument (BD Bioscience).

(6) In Vivo Expansion of NK Cells in NSG Mice

PBMCs, either freshly thawed or pre-activated for two days with 200 μg/mL PM21 and 100 U/mL IL-2, were washed twice and resuspended in phenol red-free RPMI media. $1\times10^5$ NK cells in a whole PBMC cell suspension were injected i.p. into NSG (NOD-scid IL-2Rgamma$^{null}$) mice. PM21-particles (amounts specified in figure legends, twice weekly) and IL-2 (1,000 U, thrice weekly) were also injected i.p. and PB was collected by cheek bleeds or cardiac puncture. Organs were collected at necropsy and were perfused to obtain single cell suspensions for analysis.

b) Results (1) Ex Vivo and In Vivo Expansion of NK Cells Derived from Healthy Donors and Leukemia Patients.

Since K562 cells engineered to express mbIL21, have been reported to have better efficiency for NK cell expansion without senescence, PM-particles were prepared from K562-mb21-41BBL cells, denoted PM21-particles. The PM21-particles were characterized for size distribution and the consistency of mbIL21 content (Figure S 1), and tested for their NK cell expansion capabilities.

Figure 1C:
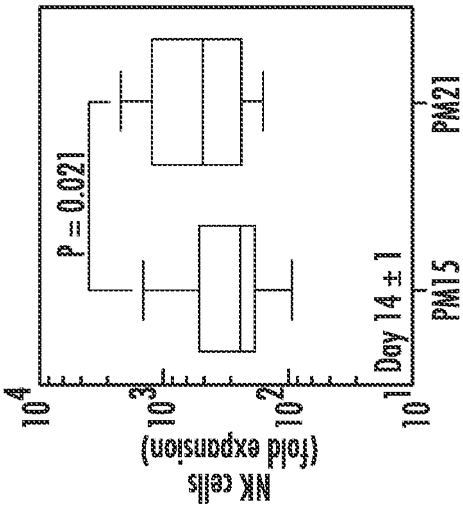

PBMCs were cultured with PM21-particles (200 μg/mL) for 28 days. NK cells stimulated with PM21-particles expanded and the content of NK cells reached>90% by day 14 in PM21-particle stimulated NK cell cultures c (FIG. 1AB). Cumulative analysis of NK cell expansions, at day 14±1 of culture, showed that PM21-particles (mean 825 fold expansion, range 163-2,216, n=13) are significantly (p=0.021) more effective as compared to PM15-particles (mean 424 fold, range 290-570, n=30) (FIG. 1C). Furthermore, NK cells stimulated with PM21-particles expanded exponentially during the period of 28 days reaching over 100,000 fold expansion, in contrast to the NK cell expansion with PM15-particles which stalled by day 22 of culture due to senescence. Thus, PM21-particles have improved NK cell expansion proficiency over the PM15-particles and the NK cell expansion with the PM21-particles was comparable to that reported with K562-mb21-41BBL feeder cells from which the PM21-particles were derived. PM21-expanded NK cells were also cytotoxic against leukemia cell lines (FIG. S2).

Figure 1D:
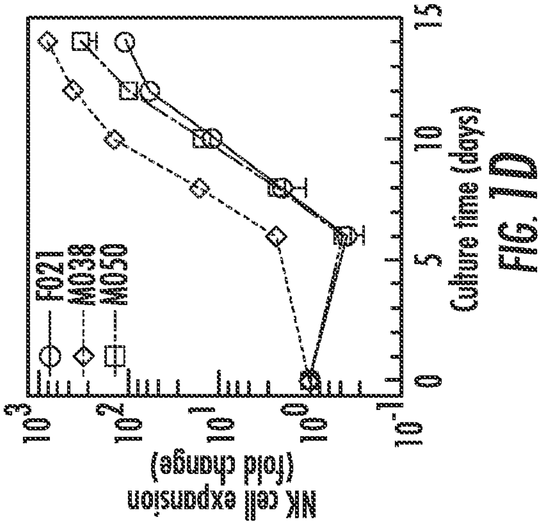
Figure 1E:
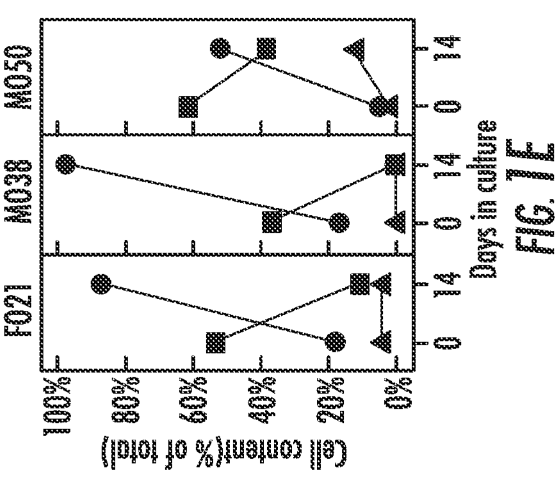

The NK cell expansion capabilities of PM21-particles were further tested with PBMCs from leukemia patients in remission. PM21-particles induced NK cell expansion relatively efficiently from all three patient derived samples in 14 days of culture (113±7 fold for F021, 810±81 fold for M038, and 352±86 fold for M050, FIG. 1D). The expansion was specific for NK cells where the percentage of NK cells respective to total $hCD45^+$ cells rose preferentially (FIG.

Figure 1F:
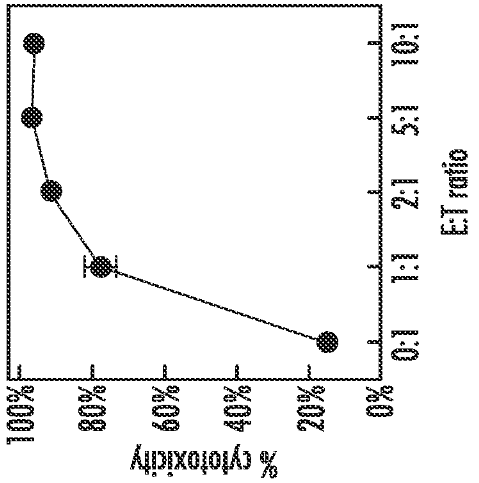

1E). For sample F021, cytotoxicity of expanded NK cells was tested in an autologous setting against tumor blasts obtained from the same patient during active disease (FIG. 1F). At a relatively low effector to target ratio (E:T) of 1:1, 78±3% of tumor cells were apoptotic. Thus this method can be used in an autologous transplant setting.

Figure 2A:
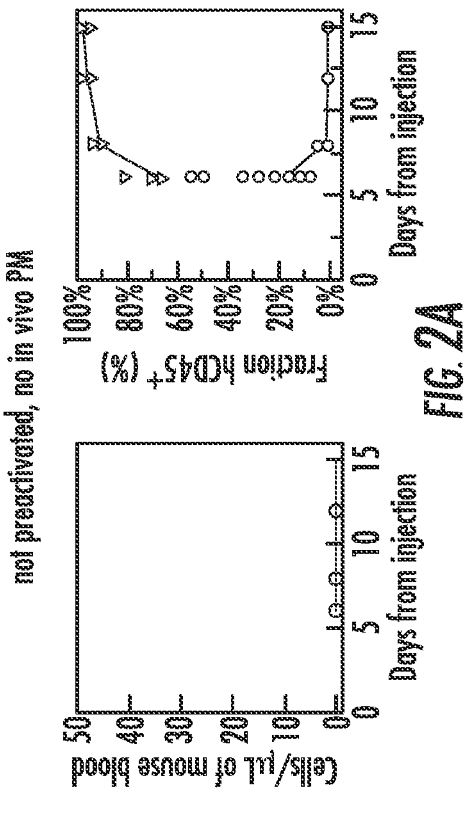
Figure 2B:
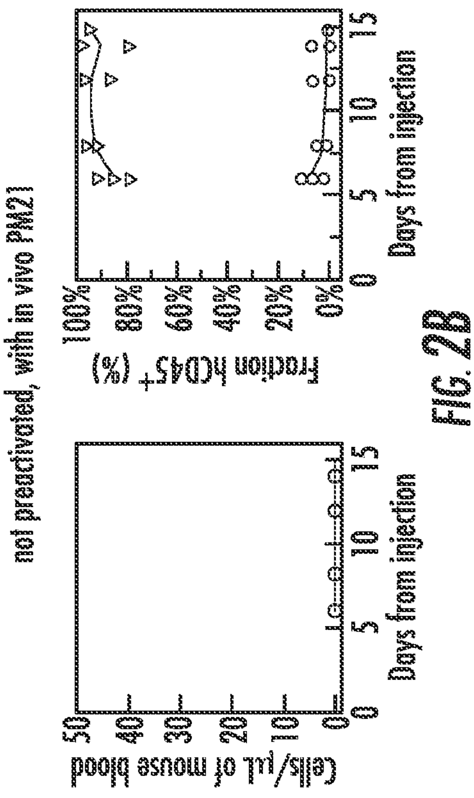
Figure 2C:
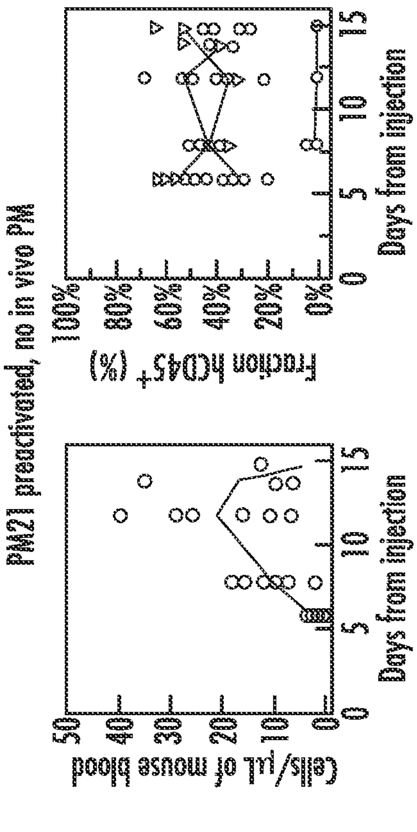
Figure 2D:
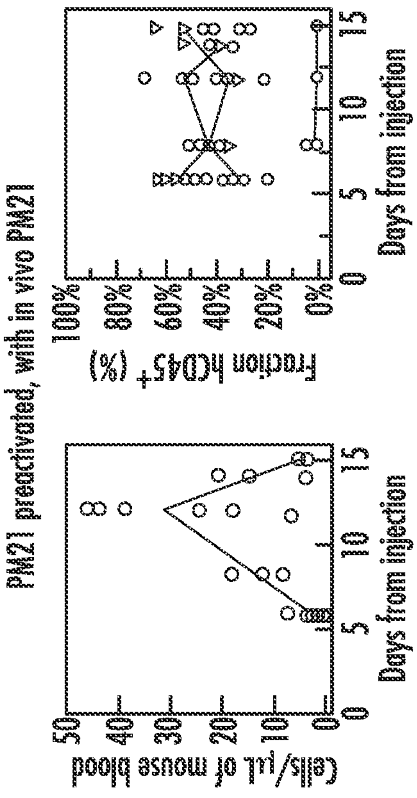
Figure 4A:
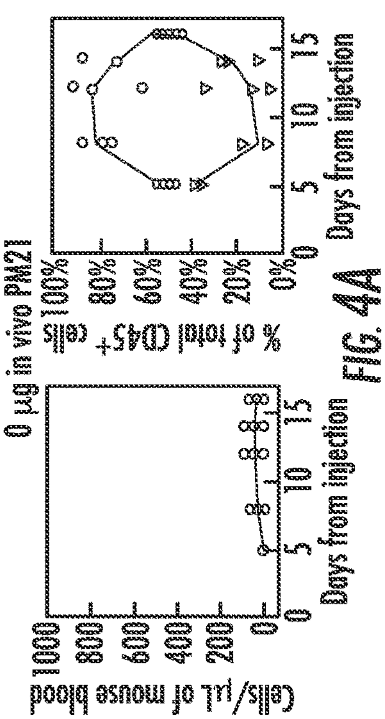
Figure 4B:
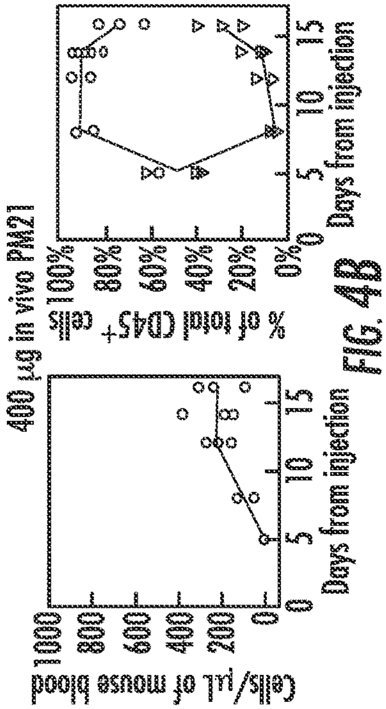
Figure 4C:
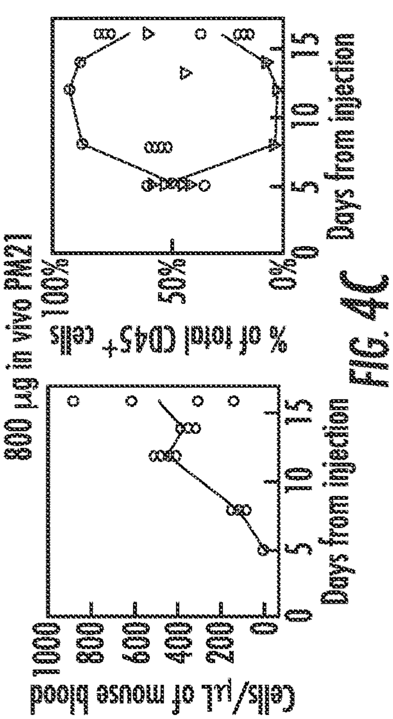
Figure 4D:
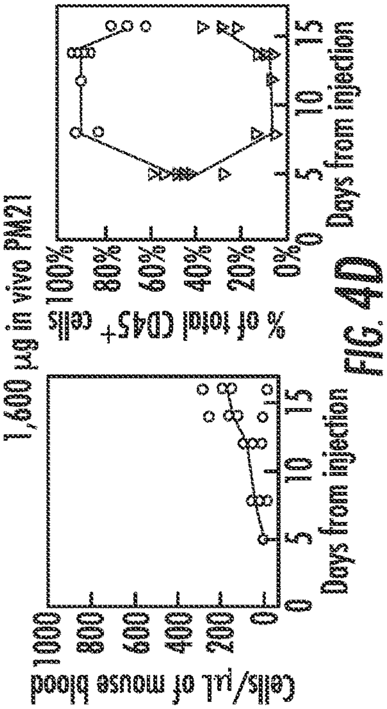
Figure 4E:
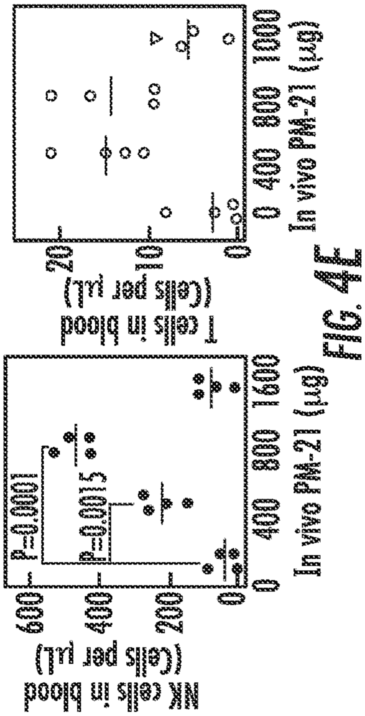

An unprecedented capability of the PM-particles is as an injectable to spur in vivo expansion. To test if PM21-particles stimulate in vivo NK cell expansion and to determine if ex vivo pre-activation is required, NSG mice were injected i.p. with $0.1\times10^{6}$ NK cells as part of either untreated PBMCs or PM21-particle pre-activated PBMCs (PM21-PBMCs). Mice injected with un-activated PBMCs had low amounts of human NK (hNK) cells in PB and only hT cells increased as a percentage of total $hCD45^{+}$ cells over 15 days post injection (FIG. 2AB). In significant contrast, PB of mice injected with PM21-PBMCs were found to have elevated amounts of hNK cells that peaked 12 days post i.p. injection (FIG. 2CD). The NK cell content enriched to 53±8% of $hCD45^{+}$ cells. In the same experiment, the efficacy was tested for in vivo i.p. application of PM21-particles to promote better in vivo NK cell expansion. For mice injected with regular PBMCs, additional in vivo PM21-particles did not stimulate hNK cell expansion. However, applying PM21-particles in vivo to mice grafted with PM21-PBMCs had an effect where hNK cell amounts were higher compared to the mice with PM21-PBMCs that did not receive in vivo PM21-particles (FIG. 2D).

To provide evidence that the PM21-particles induce in vivo NK cell proliferation, analysis was performed with CTViolet labeled hNK cells expanding in vivo at 6 days post i.p. inoculation. The cells from mice injected with un-activated PBMCs showed none or very little decrease in the CTViolet fluorescence, indicating that there was none or very few cell divisions of NK cells (FIG. 3 AB). The hNK cells from mice injected with PM21-PBMCs showed significant diminishment of the CTViolet fluorescence intensities (FIG. 3 CD). Fitting of the fluorescence intensities showed that the intensity decrease correlates with the major population, dividing 7 cell divisions in vivo within 6 days. For the hNK cells obtained from mice that received i.p. injections of PM21-particles, one more division can be observed. This additional doubling with administration of the in vivo PM21-particles correlates with the higher NK cell amounts observed in PB with in vivo PM21-particles.

To further verify if in vivo PM21-particles enhance in vivo NK cell expansion, a dose dependence of in vivo PM21-particles was studied (FIG. 4). A dose dependent increase in hNK cells in PB was observed from 0 to 800 μg of PM21-particles per injection (FIG. 4E). At a dose of 800 μg (corresponding to about 100 ng of mbIL21), 470±40 hNK cells per μL of PB was observed at 12 days after i.p. injection of the PM21-PBMCs. This NK cell concentration in PB was 5 fold higher than the concentration that is generally thought to be therapeutically efficacious in an AML setting. The dose dependent effect for in vivo expansion was specific for hNK cells where T cell amounts did not increase significantly (FIG. 4E). At a higher amount of 1,600 μg per injection, PB hNK cell amounts diminished, similar to the effect observed ex vivo where ~200-400 μg/mL is optimal for PM21-particles or PM15-particles and higher amounts attenuated NK cell expansion.

Figure 5:
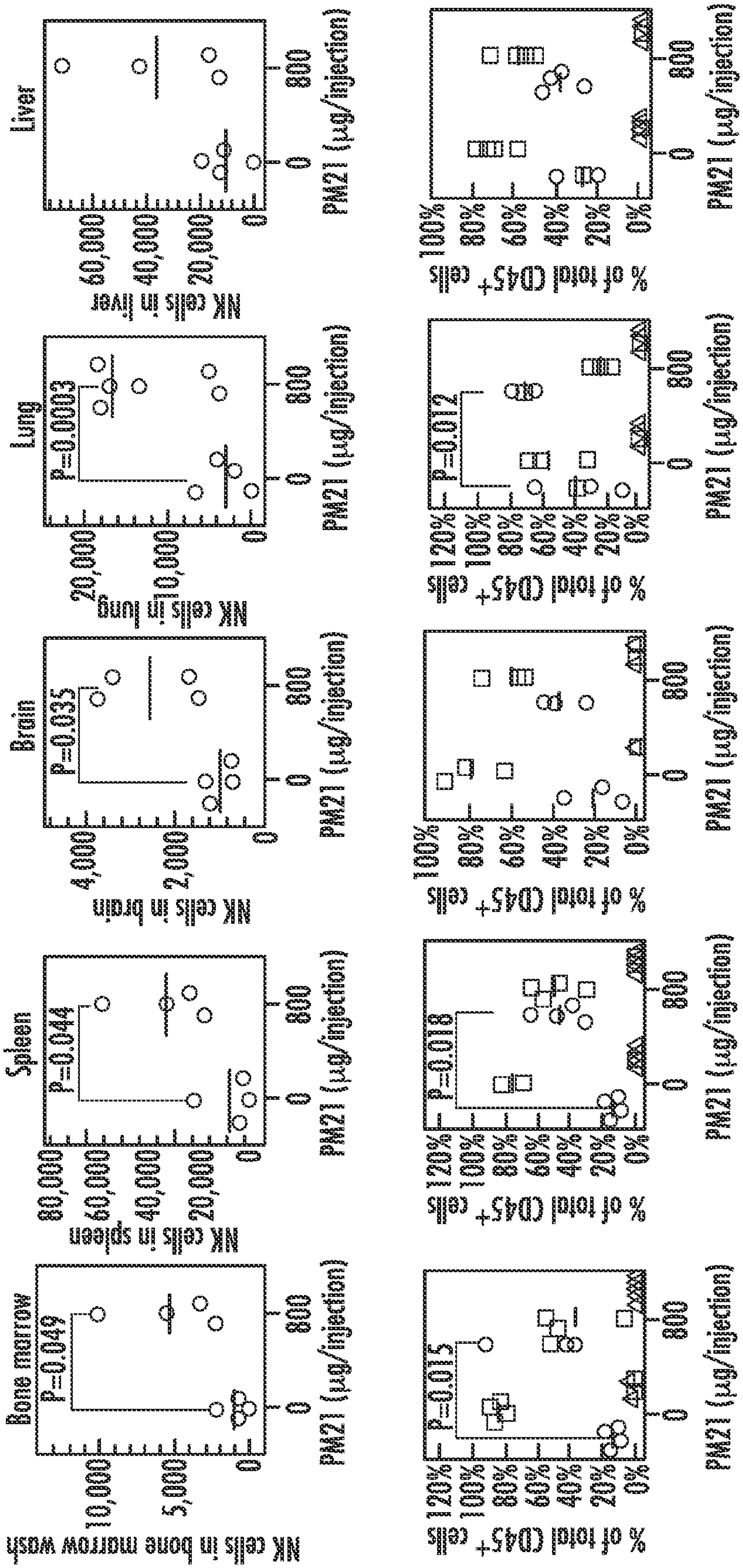
Figure 6A:
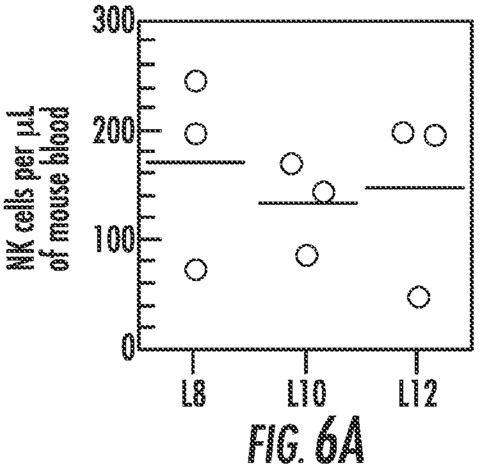
Figure 6B:
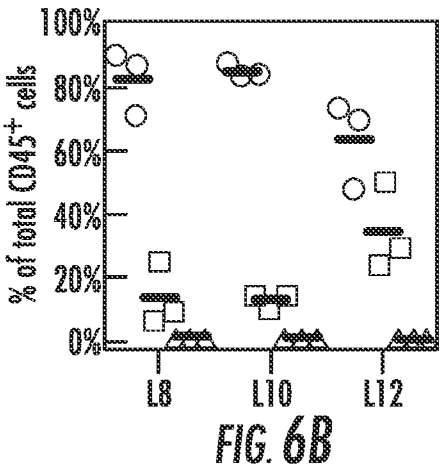
Figure 6C:
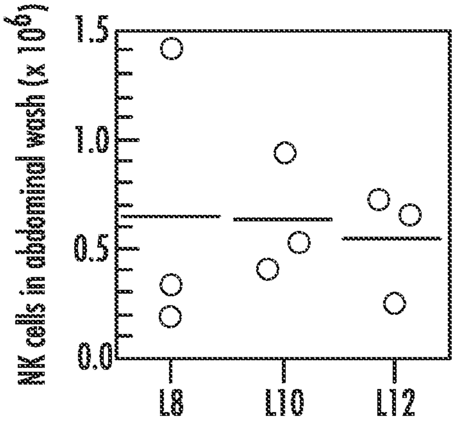
Figure 6D:
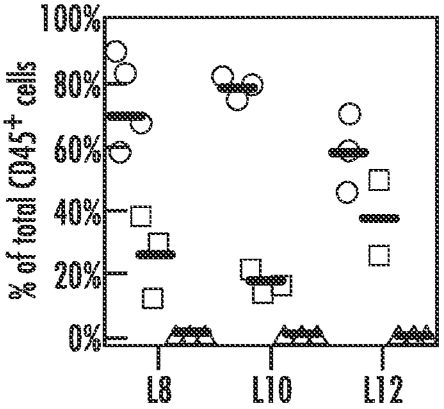

The observation of significant amounts of hNK cells in PB shows that hNK cells expanding in the i.p. injected PM21-PBMCs can migrate out from the abdominal cavity to the PB. To verify that the adoptively transferred hNK cells can migrate to potential sites of disease, hNK cells in various organs were quantified (FIG. 5). Human NK cells were found in every organ inspected, and higher amounts of hNK cells were found in organs from mice treated in vivo with 800 μg of PM21-particles, all significantly ($p<0.05$) except in livers. Furthermore, the organs from the mice treated with 800 μg of PM21-particles had higher percentage of hNK cells as a fraction of total $hCD45^{+}$ cells.

The mice based studies described here showed that the procedure combining ex vivo short pre-activation with PM21-particles and in vivo administration of PM21-particles induces significant in vivo NK cell expansion, potentially in the therapeutically relevant range. To show consistency, necessary for clinical use, the procedure was applied to leukocyte sources from three different donors (different from those used in other experiments) (FIG. 6). The average amount of hNK cells in both PB and abdominal wash was relatively consistent between leukocyte sources. The percentage of hNK, hT cells and other $hCD45^{+}$ cells were also very consistent for mice within the group injected with the PM21-PBMCs from a particular leukocyte source (n=3) and also between leukocyte sources L8 and L10.

(2) Phenotype of NK Cells Expanded with PM21-Particles.

The anti-tumor cytolytic activity of NK cells are determined by the balance of stimuli from activating and inhibitory signals. Here, a detailed comparative inspection was performed for the PM21-particle stimulated NK cells 1) expanded ex vivo with PM21 for 12 days, 2) expanded in vivo and isolated from PB, and 3) expanded in vivo and isolated from the abdominal wash (AW). These comparisons are made using cells from a single donor in all of the settings and performed in parallel (FIG. S3).

Presence of CD16, the Fcγ receptor, on NK cells is required for effective antibody dependent cytotoxicity (ADCC). Nearly all NK cells from in vivo expansion show expression of CD16 (97% and 87% for PB and AW, respectively). CD94 is a surface receptor that forms heterodimeric complexes with NKG2C or NKG2A. About half of the NK cells expanded ex vivo have CD94 expression. For NK cells expanded in vivo, cells from the AW (64±9%) have higher expression than NK cells from PB (38±13%). Receptors of the NKG2 family both bind to CD94, inclusive of NKG2C as an activating receptor and NKG2A as an inhibitory receptor. The ex vivo expanded NK cells had relatively low expression of NKG2C, but NK cells from the AW were higher (53±8%) and higher yet for NK cells from PB (61±2%). The fraction of NK cells that express NKG2A were higher in the AW (82±8%) than PB (67±12%) and those from ex vivo expansion (74%). NKG2D is another important activating receptor found on NK cells and its expression was found on 61±6% of AW NK cells, 26±3% from PB and about 75% of NK cells expanded ex vivo. The expression of CD62L, known to be correlated with marrow homing, was higher for NK cells in PB (63±10%) and lower for that in the AW (39±14), which is consistent with the expression being higher on cells that were mobilized. NKp44 and NKp46 are members of the natural cytotoxicity receptor family and play a role in NK cell mediated cytolysis. NKp46 was expressed on NK cells from both PB (76±9%) and AW (89±5%). NKp44 was relatively not well expressed in these NK cells from all the sources. On the other hand, NKp46 was well expressed from both PB (89±5) and AW (76±9). TRAIL is a ligand on NK cells that induces apoptosis of targets via the death receptor pathway. TRAIL was expressed on 36±6% of NK cells from AW, 20±4% of PB and 26% of ex vivo expanded cells. KIR2D is the killer immunoglobulin-like receptor (KIR) 2D subtype and a minority (about ⅓) of the NK cells from in vivo or ex vivo expressed KIR2D. The proportion of CD8 and CD4 T cells were analyzed and found that CD8 T cells were more abundant than CD4 T cells from the in vivo samples. The presence of NK suppressive Treg cells was also probed and very few (<0.1% of all $CD3^+$ cells) were observed in in vivo samples.

c) Discussion (1) PM21-Particles Facilitate Ex Vivo and In Vivo NK Cell Expansion to Therapeutically Relevant Amounts.

Adoptive NK cell therapy holds high promise as a cancer therapy for initial treatment and remission maintenance of various tumors. A requirement for therapeutic use of NK cells is a method for rapid and selective NK cell expansion that is safe, simple, and overall therapeutically effective. Several cytokine and feeder cell based methods are currently being clinically investigated and the methodology using K562-mb21-41BBL cell line is among the most effective for ex vivo NK cell expansion. While feeder cell methods are effective for providing a high initial dose and can allow for multiple dosing, the ability of the ex vivo expanded NK cells for homing to the bone marrow, important for leukemia treatment, can be affected and the in vivo persistence of the infused NK cells may not be optimal. The combined ex and in vivo PM21-particle based NK cell expansion method described here can significantly enhance the efficacy of NK cell adoptive therapy.

Importantly, PM21-particles can be used for in vivo stimulation to promote in vivo expansion and persistence. The methodology developed here used a short 2 day ex vivo pre-activation, followed by in vivo administration of PM21-particles. In vivo application of the PM21-particles induces higher in vivo NK cell expansion, dose dependent on the in vivo applied PM21-particles. With the current optimized procedure, an average 360-fold in vivo increase of PB NK cells was observed between days 5 to 12 after i.p. injection of PM21-PBMCs, and perhaps greater fold of expansion in the intraperitoneal cavity. For comparison, it was shown in a recent study that following i.v. infusion of 1-2×$10^6$ NK cells only about 5 to 17 NK cells per μL of blood were observable on day 14 after infusion. In contrast, in this study using PM21-particles stimulation, it has been observed that >400 NK cells/μL of blood on day 12 after i.p. infusion of 2.0×$10^6$ PM21-PBMCs (11%, i.e. 0.2×$10^6$ NK cells). Also, the former study used 5 μg (~50,000 U) per injection (thrice weekly) of either IL-2 or IL-15, whereas a relatively low dose of IL-2 (1,000 U/injection, thrice weekly) was used in the study. In a different study, 30×$10^6$ NK cells, preferentially expanded ex vivo with K562-mb15-41BBL feeder cells, were injected i.v. followed by tracking the injected human lymphocytes using anti-CD45 antibody (not by a combination of anti-CD56 and anti-CD3). With their method, high dose of i.p. injected IL-2 (25,000 U/daily) was required for lymphocyte persistence, with the NK cell concentrations not determined but rather implied. In comparison to these previous methods, the magnitude of PM21-particle stimulated in vivo NK cell expansion is unprecedented and is a unique capability of the PM21-particles Here, the route of delivery of the PM21-PBMCs to NSG mice was by i.p. injection, similar to previous pre-clinical studies. In comparison to these previous studies, the PM21-particle based method is advantageous in several aspects. First, combined ex vivo pre-activation and in vivo stimulation with PM21-particles enables the use of a much smaller amount of unselected PBMCs compared to cytokine activation of isolated NK cells, which requires collection of a large amount of lymphocytes by apheresis followed by extensive laboratory processing for NK cell enrichment. Second, the PM21-particle based method only requires a short 2 day pre-activation, instead of two week culture based expansion, that can allow for better preservation of physiologically relevant functionality. Third, the current method allows for far greater in vivo expansion compared to previous methods that do not allow expansion or in vivo persistence without the use of high dose IL-2, which has been associated with clinical toxicity. For intraperitoneal tumors, the advantages of the currently described method can significantly enhance the overall anti-tumor effect. In the absence of intraperitoneal tumors, the intraperitoneal cavity can provide a hospitable environment by confining the PM21-particle to this volume to foster good in vivo expansion, clearly shown by proliferation analysis with CTViolet, and then the NK cells can migrate out at significant amounts to the PB and organs. NK cells were not only observed in PB, but were found in organs and also were more abundant with in vivo application of PM21-particles. The NK cell amounts measured in bone marrow are comparable to those in a study using NK cells generated from $CD34^+$ umbilical cord blood stem cells, indicating that these NK cells are competent for marrow homing.

Phenotyping of NK cells expanded in parallel ex vivo or in vivo (FIG. S3) indicated that the resulting cells were similar, irrespective of the approach. Interesting differences were observed with respect to expansion of $NKG2A^-$ and $NKG2C^+$ subpopulations that were mostly observed with NK cells expanded in vivo but not in ex vivo settings. $NKG2C^+$ NK cell populations have been observed during viral reactivation, associated with "memory-like" response and were recently shown to be dependent on monocytes for production of IL-12. Presence of $NKG2C^+$ NK cells in patients with CMV reactivation after stem cell transplantation for AML was also associated with better outcomes and less relapse. Also, the existence of significant population of $NKG2A^-$ NK cells that are resistant to HLA-E induced inhibition can be important in treatment of multiple myeloma patients where cells downregulate HLA class I but express HLA-E to evade NK cells response. Approaches aimed at downregulation of NKG2A have been proposed as a means to improve NK cell cytotoxicity and thus their therapeutic potential. Since ex vivo expanded cells were mostly $NKG2A^+$, shortening the time of ex vivo culture with subsequent in vivo expansion can provide additional benefit in generation of NK cells with greater phenotypic diversity and potentially good cytotoxicity against targets.

(2) Potential Clinical Utility of PM21-Particles.

The capabilities of PM21-particles for NK cell expansion can allow wider use of adoptive NK cell therapy for cancer treatment and potentially for other maladies as well. The PM21-particles can easily be substituted for the feeder cells currently used in clinical trials to ease logistics and mitigate risks. For regulatory jurisdictions where the use of tumor derived feeder cells are prohibited or approval is difficult to obtain, the PM21-particles are a ready solution for ex vivo expansion and activation. For use of PM21-particles for ex vivo expansion in an allogeneic setting, T cell depletion can be performed prior to ex vivo NK cell expansion. Current clinical trials of NK cells grown with K562-mbIL21 utilize T cell depletion prior to NK cell expansion to eliminate allogeneic T cells that may cause GvHD. Moreover, in vivo administration of the PM21-particles can further expand the NK cells in vivo, an unprecedented capability, and possibly diminish T cell expansion to mitigate GvHD. For treatment of peritoneal cancer and other intraperitoneal tumors such as in persistent ovarian epithelial cancer or desmoplastic small-round-cell tumor, this NK cell expansion method can be clinically translated. Anti-tumor efficacy experiments for elimination of intraperitoneal tumor are currently underway. Usage of PM21-PBMC and PM21-particles for autologous treatment is possible and methodologies for incorporating T cell depletion are being explored for application in an allogeneic setting.

Importantly, the NK cells expanded by this method bio-distribute out from the abdominal cavity to peripheral blood and multiple organs that are potential sites of various other cancers. While the i.p. route of injection is unconventional for treatment of hematological malignancies, delivery of NK cells by this i.p. path results in PB concentration of NK cells that is relevant for AML treatment.

The particle based approach for NK cell specific signaling can be a platform to include other signaling molecules or even a vehicle for packaged delivery of agents for further targeted stimulation of NK cells to enhance homing, anti-tumor cytotoxicity and persistence. The PM21-particles can be highly complementary with all the innovative NK cell specific immunotherapy methods (check point inhibitors, CARs, bispecific engagers (BiKE), DT fused IL-2 for Treg depletion, etc.) being developed and with the beneficial effects being compounded upon in vivo expansion of NK cells with PM21-stimulation. Even as a pre-clinical utility, the currently described method can allow an unprecedented method to study such combination methods. While of course there are murine models, there are no other methods to study human NK cells that can be present in vivo for a significant duration.

To summarize, this procedure with PM21-particles allows in vivo preferential NK cell expansion at levels typically only achieved with ex vivo expansion with feeder cells, but without the need of cell culture with feeder cells or high cytokine doses that are toxic. Furthermore, PM21-PBMCs with in vivo delivery of PM21-particles can be used in autologous settings, to take advantage of beneficial synergistic effect of other immune cells on NK cell function and further combined with other strategies such as anti-KIR antibodies or BiKEs to maximize NK cell cytotoxicity. Thus this method meets the criteria for generation of NK cells for potential therapeutic efficacy while being simple, more amenable for clinical translation, and can be impactful for treatment of cancer or other maladies.

2. Example 2: Bone Marrow Trafficking of NK Cells Through Stimulation of Fucosylation by PM21 Particles PM21-particles prepared from K562 cells transformed to express engineered membrane bound form of IL-21 and 41bbl (K562.mb21.41bbl) induces efficient specific expansion of NK cells. Stimulation provided by PM21-particles or K562.mb21.41bbl used as feeder cells (FC21) in co-culture with NK cells induces full fucosylation of sLex, observed by HECA-452 mAb binding by flow cytometry.

NK cells were expanded by PM21 or FC21 and were stained with HECA452 mAb and analyzed by flow cytometry. HECA452 specifically recognizes the fucoyslated form of PSGL-1, CD44 and other E-selectin ligands. NK cells stimulated with PM21 or FC21 had significantly higher MFI by flow cytometry analysis compared to untreated NK cells, NK cells treated with soluble cytokines, or NK cells treated feeder cells having only mbIL21 (but not 41bbl). This highly indicates that stimulation with PM21 particles and/or FC21 feeder cells can drive the trafficking of NK cells to the bone marrow and that the bone marrow trafficking of therapeutic NK cells produced through stimulation with PM21 or FC21 can improve bone marrow and improve treatment of bone marrow born malignancies.

Figure 7:
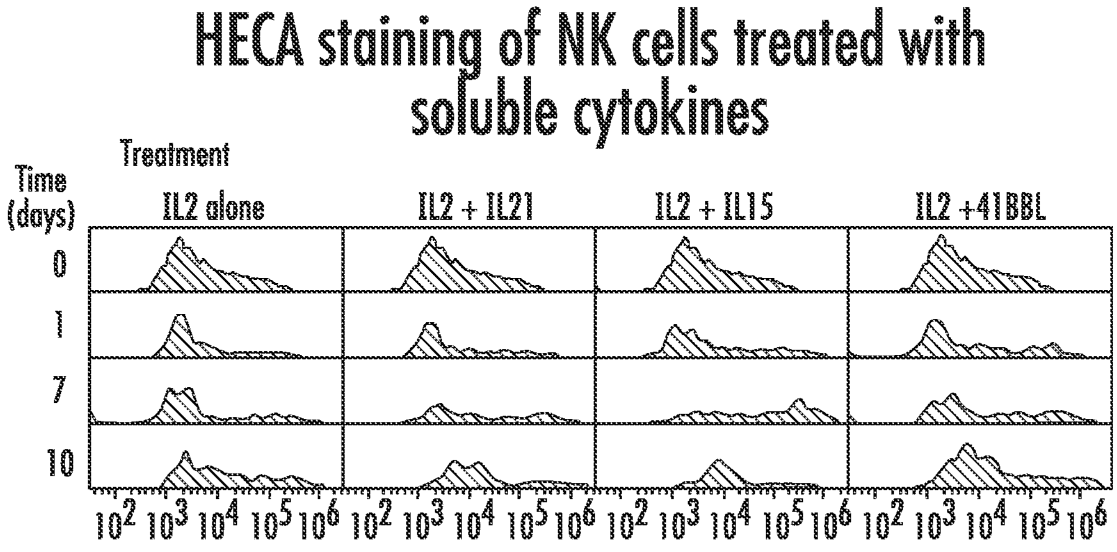
FIG. 7 shows HECA-452 staining of NK cells treated with soluble cytokines at 0, 1, 7, and 10 days of stimulation.
Figure 8:
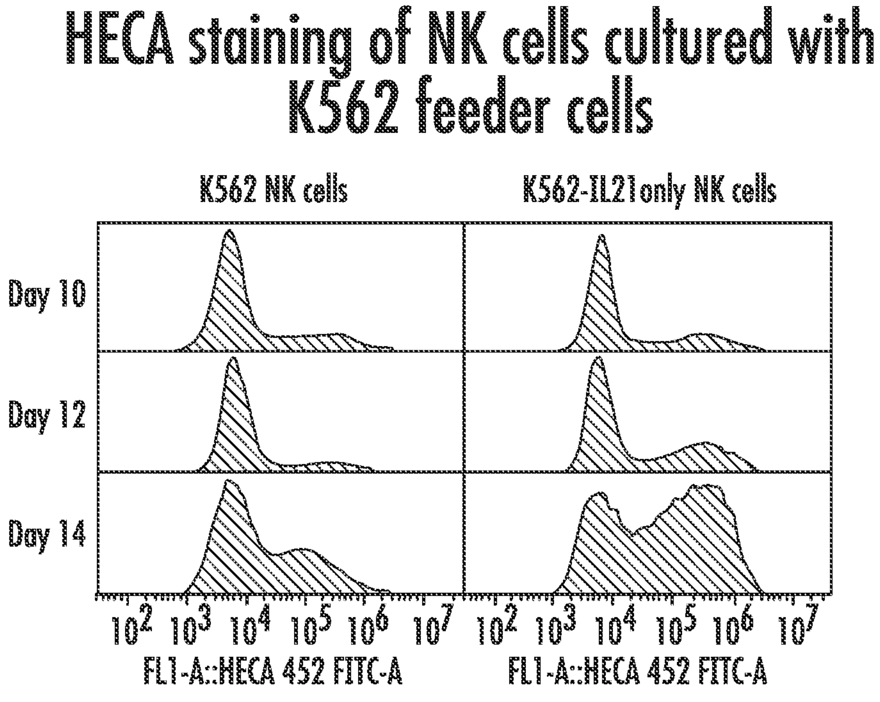
FIG. 8 shows HECA-452 staining of NK cells cultured with K562 feeder cells following 10, 12, and 14 days of stimulation.
Figure 9:
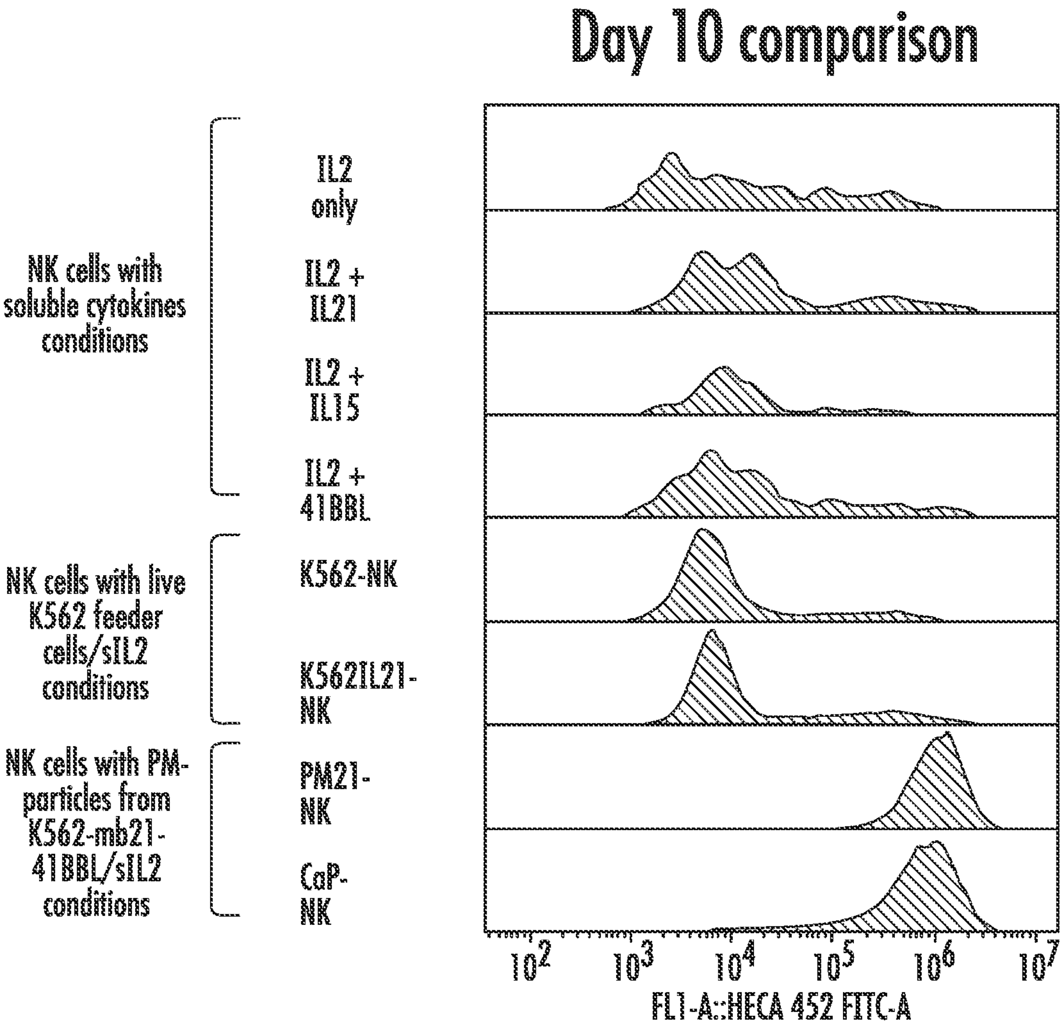
FIG. 9 shows a HECA-452 staining comparison of NK cells stimulated under various conditions following 10 days of stimulation.
Figure 10:
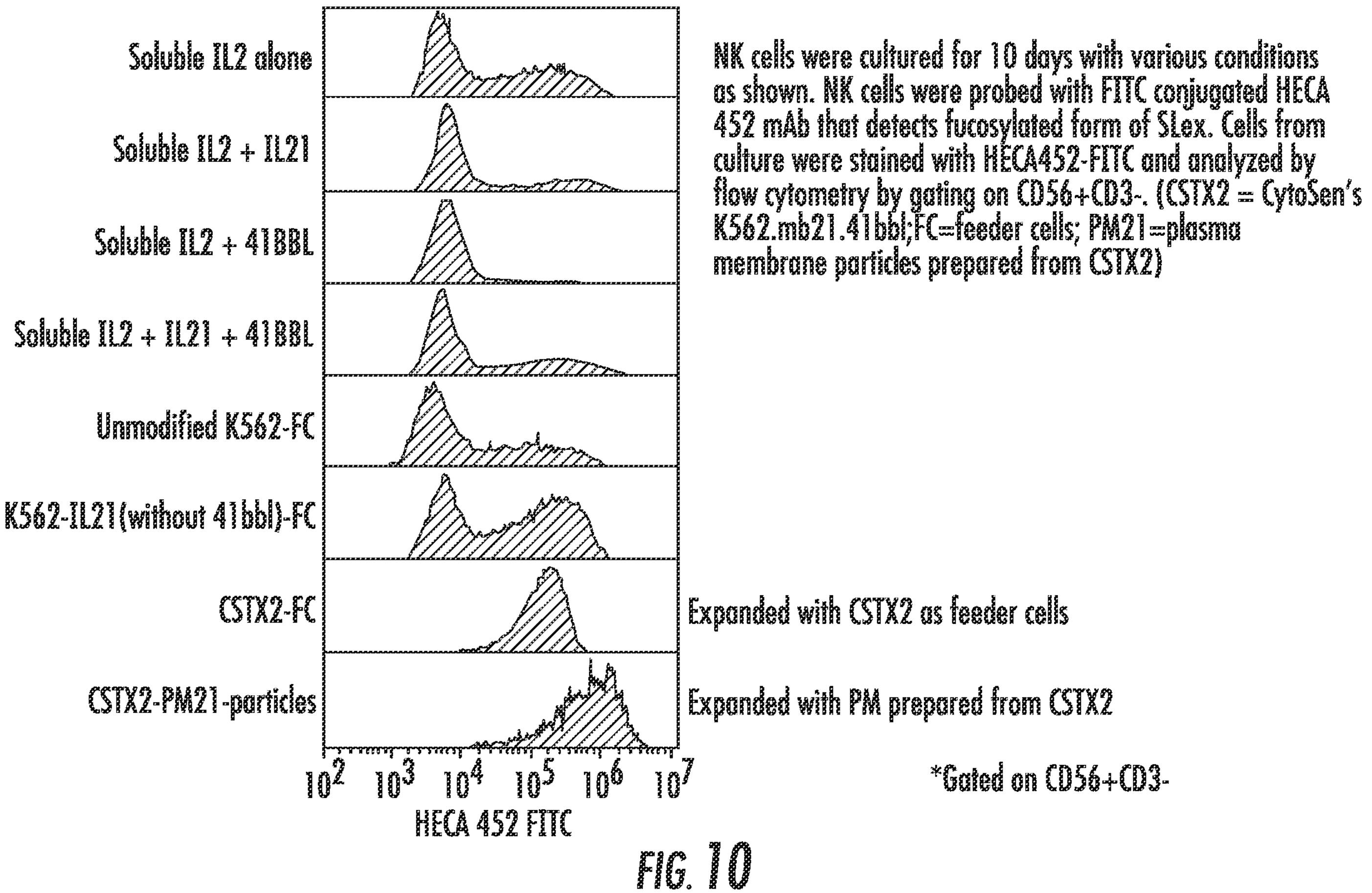
FIG. 10 shows HECA-452 staining on NK cells cultured under various conditions following 10 days of stimulation.
Figure 13A:
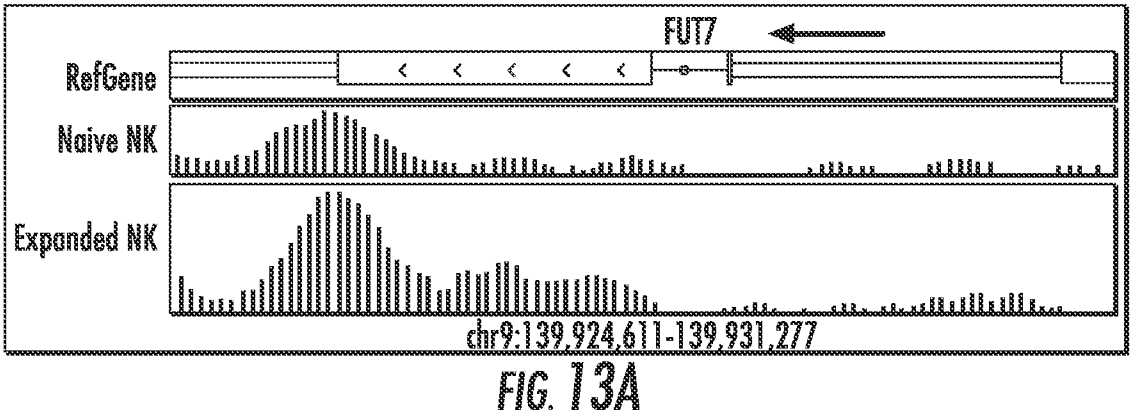
Figure 13B:
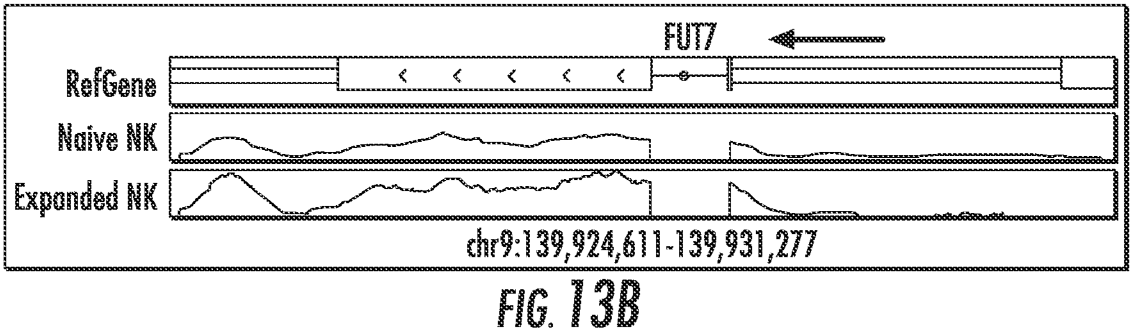
Figure 13C:
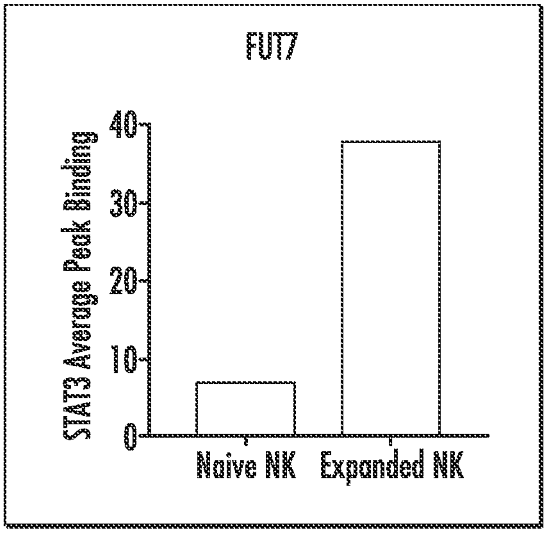
Figure 13D:
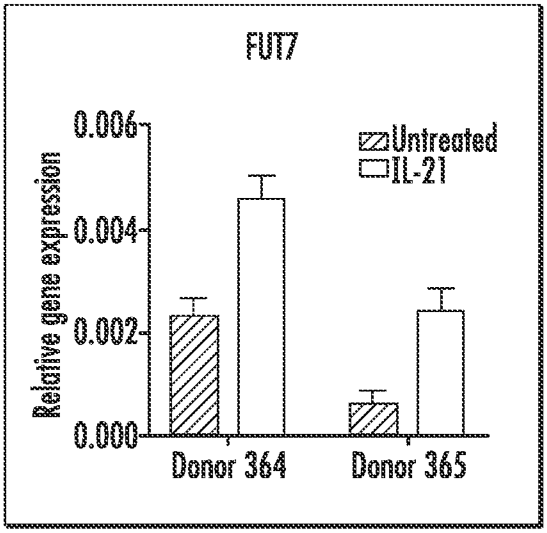

FIG. 7 shows the effect of soluble cytokines on HECA452 staining of NK cells following 0, 1, 7, and 10 days of stimulation. The effect of particle or feeder cell stimulation is shown in FIG. 8 where NK cells stimulated K562 cells or K562 cells with membrane bound IL-21 and 41BBL (FC21 cells or PM21 particles) for 10, 12, or 14 days and HECA452 stained. NK cells stimulated with K562 derived FC21 feeder cells or PM21 particles showed marked activation relative to NK cells stimulated with K562 feeder cells without IL-21. FIGS. 9 and 10 shows the effect of 10 days of culture using various conditions on NK cells. NK cells were cultured for 10 days with various conditions as shown. NK cells were probed with FITC conjugated HECA 452 mAb that detects fucosylated form of SLex. Cells from culture were stained with HECA452-FITC and analyzed by flow cytometry by gating on CD56+CD3−. (CSTX2=CytoSen's K562.mb21.41bbl; FC=feeder cells; PM21=plasma membrane particles prepared from CSTX2).

To see the effect that a rest period would have on stimulated NK cells (FIG. 11), NK cells were cultured for 10 days with CSTX2-PM21-particles (top) and then "rested" in culture for 3 days after removing PM21-particles (bottom). NK cells were probed with FITC conjugated HECA 452 mAb that detects fucosylated form of SLex. Cells from culture were stained with HECA452-FITC and analyzed by flow cytometry by gating on CD56+CD3−. (CSTX2=CytoSen's K562.mb21.41bbl; FC=feeder cells; PM21=plasma membrane particles prepared from CSTX2).

The NK cells having been stimulated with PM21 particles are stable and survived a freeze thaw process with no discernible effect on the cells (FIG. 12). NK cells were isolated from PBMCs (top), then cultured for 10 days with CSTX2-PM21-particles (middle), and then cryopreserved and thawed (bottom). NK cells were probed with FITC conjugated HECA 452 mAb that detects fucosylated form of SLex. Cells from culture were stained with HECA452-FITC and analyzed by flow cytometry by gating on CD56+CD3−. (CSTX2=CytoSen's K562.mb21.41bbl; FC=feeder cells; PM21=plasma membrane particles prepared from CSTX2).

E. References

Altvater B, Landmeier S, Pscherer S, Temme J, Schweer K, Kailayangiri S, et al. 2B4 (CD244) signaling by recombinant antigen-specific chimeric receptors costimulates natural killer cell activation to leukemia and neuroblastoma cells. Clin Cancer Res 2009; 15:4857-66.

Bachanova V, Cooley S, Defor T E, Verneris M R, Zhang B, McKenna D H, et al. Clearance of acute myeloid leukemia by haploidentical natural killer cells is improved using IL-2 diphtheria toxin fusion protein. Blood 2014; 123:3855-63.

Berg M, Lundqvist A, McCoy P, Jr., Samsel L, Fan Y, Tawab A, et al. Clinical-grade ex vivo-expanded human natural killer cells up-regulate activating receptors and death receptor ligands and have enhanced cytolytic activity against tumor cells. Cytotherapy 2009; 11:341-55.

Cany J, van der Waart A B, Tordoir M, Franssen G M, Hangalapura B N, de Vries J, et al. Natural killer cells generated from cord blood hematopoietic progenitor cells efficiently target bone marrow-residing human leukemia cells in NOD/SCID/IL2Rg(null) mice. PLoS One 2013; 8:e64384.

Carlsten M, Childs R W. Genetic Manipulation of NK Cells for Cancer Immunotherapy: Techniques and Clinical Implications. Front Immunol 2015; 6:266.
Chang Y H, Connolly J, Shimasaki N, Mimura K, Kono K, Campana D. A chimeric receptor with NKG2D specificity enhances natural killer cell activation and killing of tumor cells. Cancer Res 2013; 73:1777-86.
Childs R W, Carlsten M. Therapeutic approaches to enhance natural killer cell cytotoxicity against cancer: the force awakens. Nat Rev Drug Discov 2015.
Davis Z B, Cooley S A, Cichocki F, Felices M, Wangen R, Luo X, et al. Adaptive Natural Killer Cell and Killer Cell Immunoglobulin-Like Receptor-Expressing T Cell Responses are Induced by Cytomegalovirus and Are Associated with Protection against Cytomegalovirus Reactivation after Allogeneic Donor Hematopoietic Cell Transplantation. Biol Blood Marrow Transplant 2015.
Denman C J, Senyukov V V, Somanchi S S, Phatarpekar P V, Kopp L M, Johnson J L, et al. Membrane-bound IL-21 promotes sustained ex vivo proliferation of human natural killer cells. PLoS One 2012; 7:e30264.
Dijkers P F, Birkenkamp K U, Lam E W, Thomas N S, Lammers J W, Koenderman L, et al. FKHR-L1 can act as a critical effector of cell death induced by cytokine withdrawal: protein kinase B-enhanced cell survival through maintenance of mitochondrial integrity. J Cell Biol 2002; 156:531-42.
Fehniger T A, Cooper M A, Nuovo G J, Cella M, Facchetti F, Colonna M, et al. CD56bright natural killer cells are present in human lymph nodes and are activated by T cell-derived IL-2: a potential new link between adaptive and innate immunity. Blood 2003; 101:3052-7.
Foley B, Cooley S, Verneris M R, Curtsinger J, Luo X, Waller E K, et al. Human cytomegalovirus (CMV)-induced memory-like NKG2C(+) NK cells are transplantable and expand in vivo in response to recipient CMV antigen. J Immunol 2012; 189:5082-8.
Foley B, Cooley S, Verneris M R, Pitt M, Curtsinger J, Luo X, et al. Cytomegalovirus reactivation after allogeneic transplantation promotes a lasting increase in educated NKG2C+ natural killer cells with potent function. Blood 2012; 119:2665-74.
Fujisaki H, Kakuda H, Shimasaki N, Imai C, Ma J, Lockey T, et al. Expansion of highly cytotoxic human natural killer cells for cancer cell therapy. Cancer Res 2009; 69:4010-7.
Geller M A, Knorr D A, Hermanson D A, Pribyl L, Bendzick L, McCullar V, et al. Intraperitoneal delivery of human natural killer cells for treatment of ovarian cancer in a mouse xenograft model. Cytotherapy 2013; 15:1297-306.
Gleason M K, Ross J A, Warlick E D, Lund T C, Verneris M R, Wiemik A, et al. CD16×CD33 bispecific killer cell engager (BiKE) activates NK cells against primary MDS and MDSC $CD33^+$ targets. Blood 2014; 123:3016-26.
Glienke W, Esser R, Priesner C, Suerth J D, Schambach A, Wels W S, et al. Advantages and applications of CAR-expressing natural killer cells. Front Pharmacol 2015; 6:21.
Klingemann H G. Cellular therapy of cancer with natural killer cells—where do we stand? Cytotherapy 2013; 15:1185-94.
Knorr D A, Bachanova V, Verneris M R, Miller J S. Clinical utility of natural killer cells in cancer therapy and transplantation. Semin Immunol 2014; 26:161-72.
Kohrt H E, Thielens A, Marabelle A, Sagiv-Barfi I, Sola C, Chanuc F, et al. Anti-KIR antibody enhancement of anti-lymphoma activity of natural killer cells as monotherapy and in combination with anti-CD20 antibodies. Blood 2014; 123:678-86.
Leclercq G, Debacker V, de Smedt M, Plum J. Differential effects of interleukin-15 and interleukin-2 on differentiation of bipotential T/natural killer progenitor cells. J Exp Med 1996; 184:325-36.
Miller J S, Rooney C M, Curtsinger J, McElmurry R, McCullar V, Verneris M R, et al. Expansion and homing of adoptively transferred human natural killer cells in immunodeficient mice varies with product preparation and in vivo cytokine administration: implications for clinical therapy. Biol Blood Marrow Transplant 2014; 20:1252-7.
Miller J S, Soignier Y, Panoskaltsis-Mortari A, McNearney S A, Yun G H, Fautsch S K, et al. Successful adoptive transfer and in vivo expansion of human haploidentical NK cells in patients with cancer. Blood 2005; 105:3051-7.
Miller J S. Should natural killer cells be expanded in vivo or ex vivo to maximize their therapeutic potential? Cytotherapy 2009; 11:259-60.
Nguyen S, Kuentz M, Vernant J P, Dhedin N, Bones D, Debre P, et al. Involvement of mature donor T cells in the NK cell reconstitution after haploidentical hematopoietic stem-cell transplantation. Leukemia 2008; 22:344-52.
Oyer J L, Igarashi R Y, Kulikowski A R, Colosimo D A, Solh M M, Zakari A, et al. Generation of highly cytotoxic natural killer cells for treatment of acute myelogenous leukemia using a feeder-free, particle-based approach. Biol Blood Marrow Transplant 2015; 21:632-9.
Park K U, Jin P, Sabatino M, Feng J, Civini S, Khuu H, et al. Gene expression analysis of ex vivo expanded and freshly isolated NK cells from cancer patients. J Immunother 2010; 33:945-55.
Phan T G, Long G V, Scolyer R A. Checkpoint inhibitors for cancer immunotherapy. Multiple checkpoints on the long road towards cancer immunotherapy. Immunol Cell Biol 2015; 93:323-5.
Rodella L, Zamai L, Rezzani R, Artico M, Pen G, Falconi M, et al. Interleukin 2 and interleukin 15 differentially predispose natural killer cells to apoptosis mediated by endothelial and tumour cells. Br J Haematol 2001; 115: 442-50.
Rolle A, Pollmann J, Ewen E M, Le V T, Halenius A, Hengel H, et al. IL-12-producing monocytes and HLA-E control HCMV-driven $NKG2C^+$ NK cell expansion. J Clin Invest 2014; 124:5305-16.
Romagne F, Andre P, Spee P, Zahn S, Anfossi N, Gauthier L, et al. Preclinical characterization of 1-7F9, a novel human anti-KIR receptor therapeutic antibody that augments natural killer-mediated killing of tumor cells. Blood 2009; 114:2667-77.
Romee R, Foley B, Lenvik T, Wang Y, Zhang B, Ankarlo D, et al. NK cell CD16 surface expression and function is regulated by a disintegrin and metalloprotease-17 (ADAM17). Blood 2013; 121:3599-608.
Ross M E, Caligiuri M A. Cytokine-induced apoptosis of human natural killer cells identifies a novel mechanism to regulate the innate immune response. Blood 1997; 89:910-8.
Sarkar S, van Gelder M, Noort W, Xu Y, Rouschop K M, Groen R, et al. Optimal selection of natural killer cells to kill myeloma: the role of HLA-E and NKG2A. Cancer Immunol Immunother 2015.
Shimasaki N, Fujisaki H, Cho D, Masselli M, Lockey T, Eldridge P, et al. A clinically adaptable method to enhance the cytotoxicity of natural killer cells against B-cell malignancies. Cytotherapy 2012; 14:830-40.

Somanchi S S, Senyukov V V, Denman C J, Lee D A. Expansion, purification, and functional assessment of human peripheral blood NK cells. J Vis Exp 2011.

West W H, Tauer K W, Yannelli J R, Marshall G D, Orr D W, Thurman G B, et al. Constant-infusion recombinant interleukin-2 in adoptive immunotherapy of advanced cancer. N Engl J Med 1987; 316:898-905.

Zhu E F, Gai S A, Opel C F, Kwan B H, Surana R, Mihm M C, et al. Synergistic innate and adaptive immune response to combination immunotherapy with anti-tumor antigen antibodies and extended serum half-life IL-2. Cancer Cell 2015; 27:489-501.

What is claimed is:

1. A method of treating a viral infection associated with the bone marrow in a subject comprising contacting NK cells in vitro or ex vivo with one or more of plasma membrane particles expressing IL-21 and 41BBL on their surface (PM21 particles) and/or feeder cells expressing IL-21 on their surface (FC21 feeder cells) for 6 to 40 days, wherein the contacting induces a cellular mechanism within NK cells to induce fucosylation of P-selectin glycoprotein ligand-1 (PSGL-1) on the NK cells' surface, and adoptively transferring the NK cells to the subject.

2. The method of claim 1, wherein the NK cells are contacted with PM21 for 6 to 40 days.

3. The method of claim 1, wherein the method induces expression of fucosyltransferase 7 (FUT7) within NK cells correlating to the fucosylation of PSGL-1 on the NK cells' surface.

* * * * *